US011077436B1

(12) United States Patent
dePillis

(10) Patent No.: US 11,077,436 B1
(45) Date of Patent: Aug. 3, 2021

(54) MAILABLE INSPECTOR COLLECTOR

(71) Applicant: Gretchen Jolie dePillis, Riverside, CA (US)

(72) Inventor: Gretchen Jolie dePillis, Riverside, CA (US)

(\*) Notice: Subject to any disclaimer, the term of this patent is extended or adjusted under 35 U.S.C. 154(b) by 0 days.

(21) Appl. No.: 17/037,331

(22) Filed: Sep. 29, 2020

(51) Int. Cl.
| *B01L 3/00* | (2006.01) |
| *A61B 5/00* | (2006.01) |
| *A61B 10/00* | (2006.01) |
| *C12Q 1/70* | (2006.01) |
| *A61B 5/097* | (2006.01) |
| *G06N 3/08* | (2006.01) |

(52) U.S. Cl.
CPC ............ *B01L 3/50* (2013.01); *A61B 5/097* (2013.01); *A61B 10/00* (2013.01); *C12Q 1/701* (2013.01); *G06N 3/08* (2013.01); *A61B 2503/40* (2013.01); *B01L 2200/087* (2013.01); *B01L 2200/185* (2013.01); *B01L 2300/02* (2013.01); *B01L 2300/12* (2013.01); *B01L 2300/16* (2013.01)

(58) Field of Classification Search
CPC .................................. B01L 3/50; A61B 5/097
See application file for complete search history.

(56) References Cited

U.S. PATENT DOCUMENTS

2015/0031035 A1\* 1/2015 Kvam ................... B01L 3/5023
435/6.12

OTHER PUBLICATIONS

Reboud, Julien et al. "Paper-based microfluidics for DNA diagnostics of malaria in low resource underserved rural communities." PNAS (2019) 116 4834-4842. (Year: 2019).\*

\* cited by examiner

*Primary Examiner* — Christopher Adam Hixson

(57) ABSTRACT

The Mailable Inspector Collector is a (1) single-use device for (2) user-friendly collection, inspection, and (3) rendering of test results to confirm or deny the presence of a pathogen using (4) Nanotechnology with an (5) portable isothermal assay methodology, which may (6) reveal results, via color change and/or fluorescence (e.g. FAM channel excitation 470 nm to 520 nm.), the presence of at least one specific pathogen. The Mailable Inspector Collector invention can be (7) administered, distributed and disposed of by leveraging a delivery infrastructure, such as that offered by the United States Postal Service (USPS), to address the following known issues: (8) Mass distribution to the public; (9) Recycling of used elements; (10) Easy non-intrusive manner whereby a Test Subject may contribute a sample; (11) Easy manner to discern test results within minutes without complex laboratory equipment; (12) Facilitate relevant data collection as well as contact tracing.

15 Claims, 13 Drawing Sheets

Figure 1:
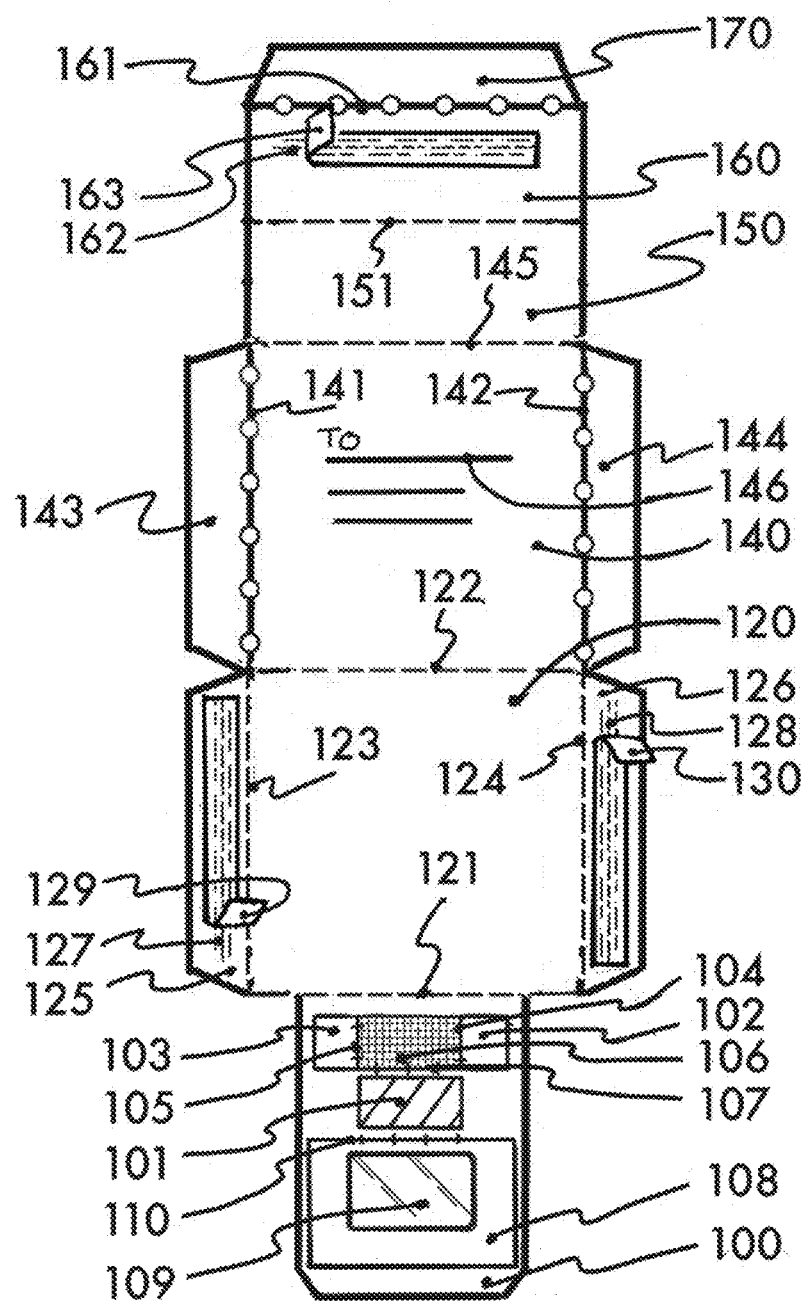

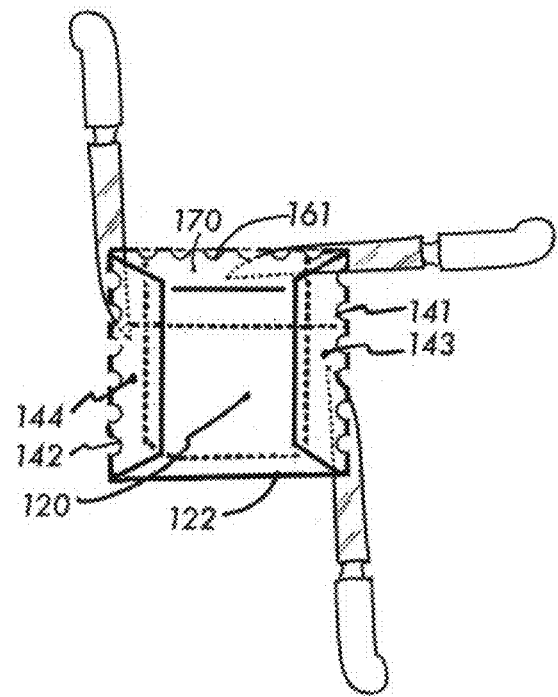
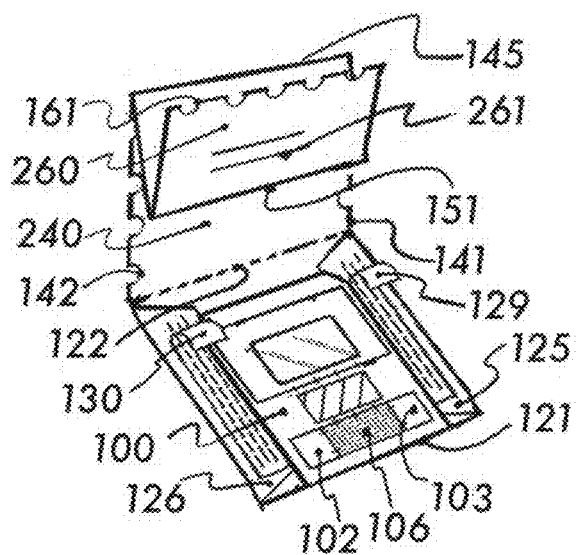

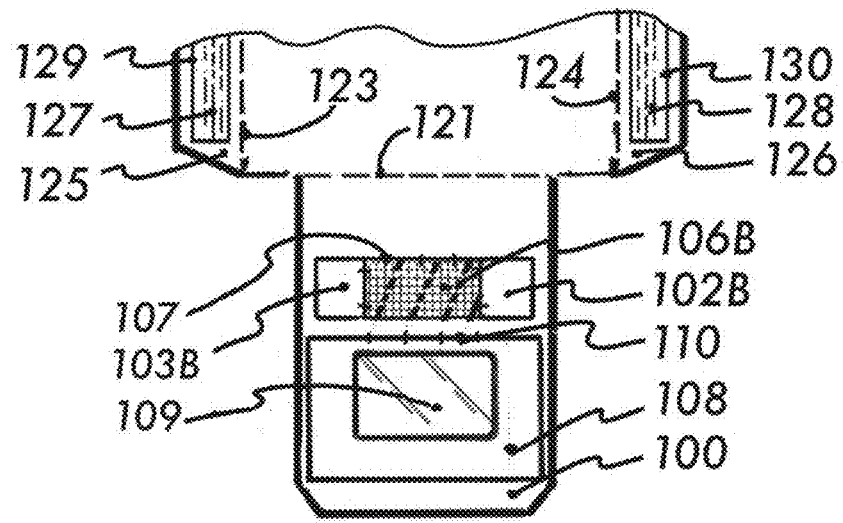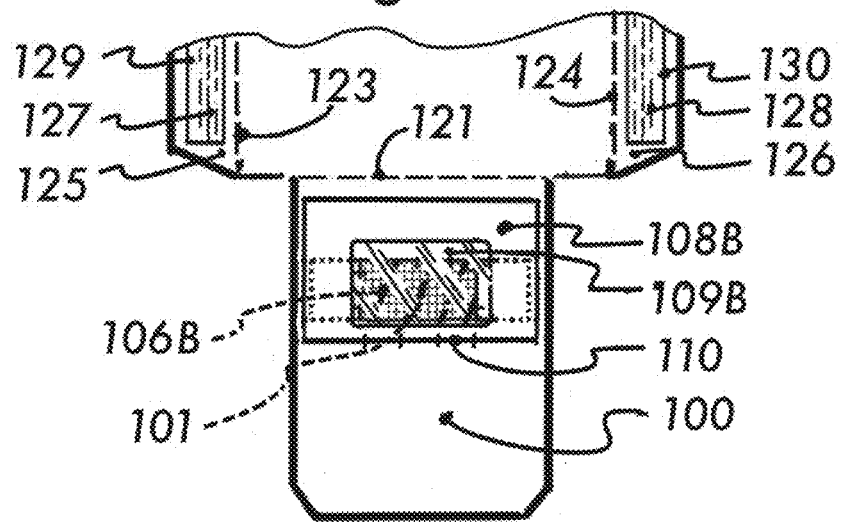

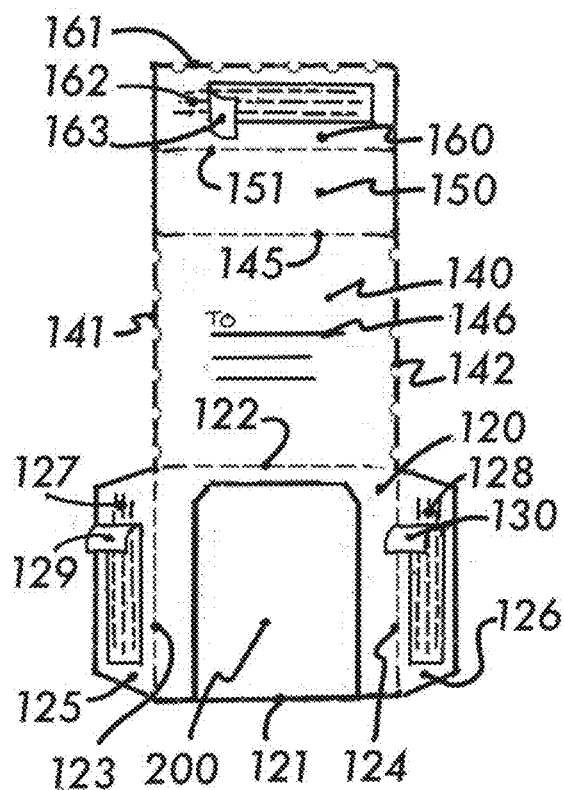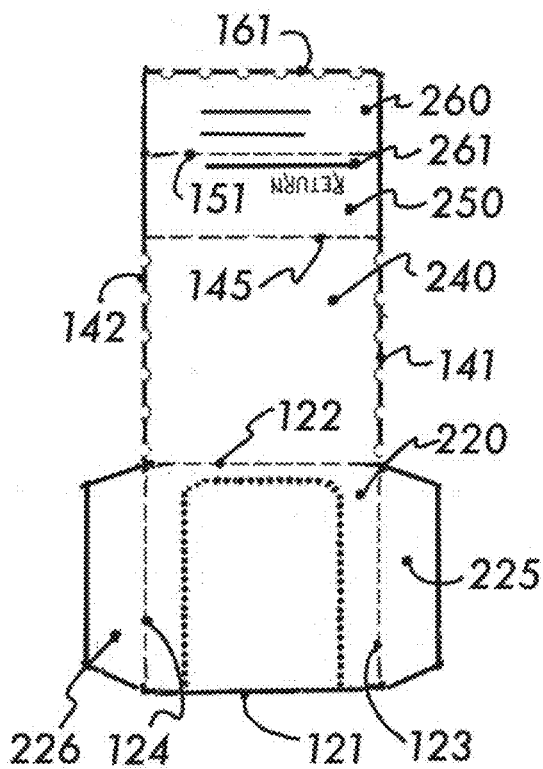

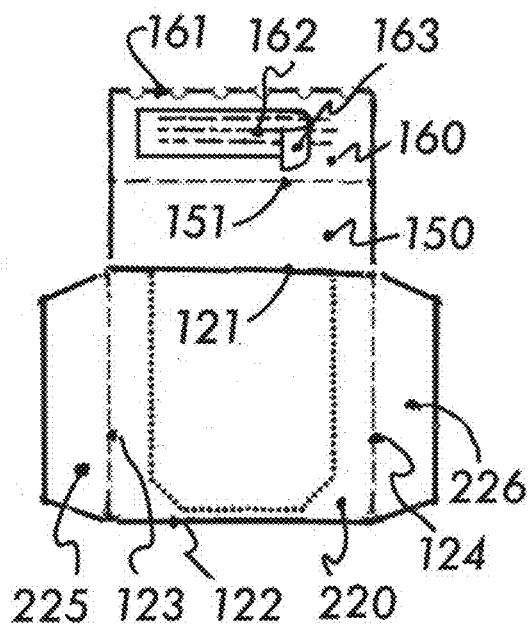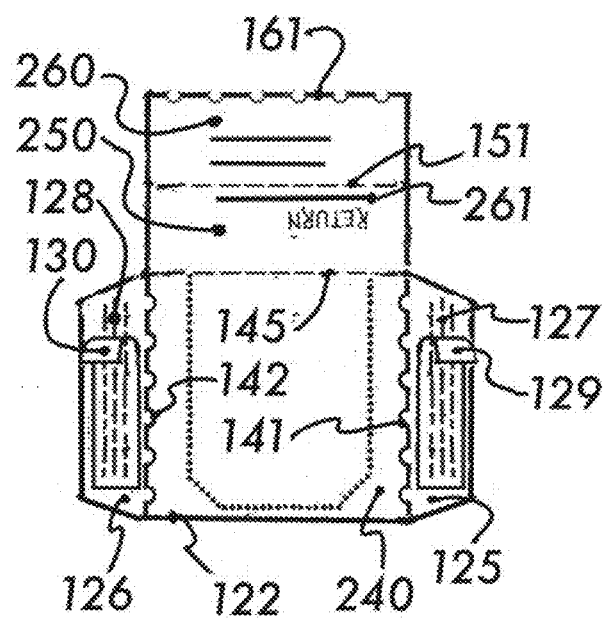

MAILABLE INSPECTOR COLLECTOR

STATEMENT REGARDING FEDERALLY SPONSORED RESEARCH OR DEVELOPMENT

The Inventor, G. J. dePillis, is not a government contractor and this device, MAILABLE INSPECTOR COLLECTOR, was not developed with any government support. The Inventor, G. J. dePillis, is not under obligation to provide any statement in accordance with 35 U.S.C. 202(c)(6) nor 37 CFR 1.77(b)(1)-(3). Reference: MPEP 310 Government License Rights to Contractor-Owned Inventions Made Under Federally Sponsored Research and Development.

CROSS-REFERENCE TO RELATED APPLICATIONS

This section does not apply. There are no other prior patent applications which could be cross-referenced. This section does not apply. This section has been completed in full. Reference: 35 U.S.C. §§ 120, 121, or 365(c), or to a provisional patent application under 35 U.S.C. § 119(e), 37 CFR § 1.76. See 37 CFR § 1.78.

This patent specification is requesting that the inventor gain exclusive rights to promote the useful art of affordable to manufacture, affordable to distribute, easy to take and interpret results, and easy to recycle or use for community data collection. This demonstrates a mechanism which is useful to the general public as per Article I, Section 8 of the Constitution which authorizes Congress to provide exclusive rights to inventors to promote the "useful arts." See Carl Zeiss Stiftungv.Renishaw PLC, 945 F.2d 1173, 20 USPQ2d 1094 (Fed. Cir. 1991).

This invention was not made with any government support and there was no contract involved. The inventor operated as an individual under their S-Corp company Pure Force Enterprises, Inc., which currently employs one individual, the owner and founder of that company, Pure Force Enterprises, Inc., and the author of this document and inventor of the device, MAILABLE INSPECTOR COLLECTOR. The government has no rights to nor in this invention in any way whatsoever. Full rights of the invention belong to the individual inventor, G. J. dePillis.

REFERENCE TO SEQUENCE LISTING, A TABLE, OR A COMPUTER PROGRAM LISTING COMPACT DISC APPENDIX

This section does not apply. All elements pertaining to the invention shall be contained herein in the documents required for application filing. No information shall be submitted on an external medium such as a compact disc.

BACKGROUND OF THE INVENTION

The field of endeavor to which the invention pertains is a mailable apparatus which can convey pathogen analysis test to a recipient and back to a recycling center in the same envelope. In this case, this apparatus can be tailored to detect corona-virus pathogen, for example. This invention was inspired to address specific problems:
1. Distribution of pathogen (e.g. virus-based particles) samples and test results
2. Distribution to the general public of device with test apparatus via delivery infrastructure.
3. Easier implementation of testing process
4. Rapid accurate results of pathogen tests
5. Enhanced efficiency in contact tracing A) EASIER DISTRIBUTION OF PATHOGEN SAMPLES AND TEST RESULTS TO GENERAL PUBLIC: At present, it is difficult to administer testing to large populations of test-eligible individuals for COVID-19
1. Need: Supply chain to support the distribution of test units.
2. Need: A test which is which is simple to administer
3. Need: A standard procedure to handle used test elements.

B) EASY TO ADMINISTER TEST: Current RT (Real Time) PCR (Polymerase Chain Reaction) test involves an invasive swab inserted up into the nose, which can be uncomfortable for the test-subject.
1. Need: A test which is easy for a human subject to take on a regular basis (if needed)
2. Need: A standard procedure whereby a sample can be collected and analyzed within a reasonable duration.
3. Need: A simple manner whereby a sample can be contributed.

C) RAPID ACCURATE RESULTS: Current RT-PCR test results are processed in an excessive duration of time. At times, the test results have an unacceptable amount of "false" results. Should a subject obtain a "false negative" result, that could mean they do not get the early treatment they genuinely need.
1. Need: A test which can return results in a reasonable amount of time
2. Need: A test whereby the results are easy to discern
3. Need: A test whereby the results are reasonably accurate
4. Need: A test which does not require complex lab equipment so that the test can be taken in rural areas, which may not have access to sophisticated lab instruments D) CONTACT TRACING: Current contact tracing, as recommended by the CDC, should be conducted for close contacts. Close contacts are defined as: any individual within 6 feet of an infected person for at least 15 minutes of laboratory-confirmed or probable COVID-19 patients. This means that tracking of infected individuals requires a more precise method whereby data is collected consistently.
1. Need: A testing unit which would support the embedding, integration, addition of an element of artificial intelligent to support the execution of contact tracing.
2. Need: A design to house the testing element to allow for nationwide delivery to an address to aid in contact tracing.
3. Need: Sufficient room in the housing of the device to allow for extra information intended for the recipient test taker to use.
4. Need: Sufficient room in the event a manufacturer would like to embed a chip for either geographic tracking or containing any other function to aid in informing the recipient, collecting data, determining location, or another useful purpose to further epidemiological, sociological, medical, neurological, or other similar useful purpose.
5. Need: Sufficient room in the device in the event a manufacturer would like to place a printed code which can be interpreted by a scanner to contain information such as medical data regarding the recipient of the unit and correlate that to a positive or negative test result.
6. Need: Sufficient room in the device in the event a manufacturer would like to print a questionnaire or survey for the recipient test-taker or their qualified trained assistant, or instructions in any language for the recipient test-taker to follow.

7. Need: A mailable unit which can be delivered in a delivery infrastructure, such as the United States Postal Service.
   a) Device delivery should comply with similar standards to which the current United States Postal Services code applies.
      For example, 39 U.S. Code § 101 Postal policy states in part:
      i. Paragraph (a) The United States Postal Service shall be operated as a basic and fundamental service provided to the people by the Government of the United States, authorized by the Constitution, created by Act of Congress, and supported by the people. The Postal Service shall have as its basic function the obligation to provide postal services to bind the Nation together through the personal, educational, literary, and business correspondence of the people. It shall provide prompt, reliable, and efficient services to patrons in all areas and shall render postal services to all communities . . .
      ii Paragraph (b) The Postal Service shall provide a maximum degree of effective and regular postal services to rural areas, communities, and small towns where post offices are not self-sustaining. No small post office shall be closed solely for operating at a deficit, it being the specific intent of the Congress that effective postal services be insured to residents of both urban and rural communities . . .
      iii. Paragraph (f) In selecting modes of transportation, the Postal Service shall give highest consideration to the prompt and economical delivery of all mail. Modern methods of transporting mail by containerization and programs designed to achieve overnight transportation to the destination of important letter mail to all parts of the Nation shall be a primary goal of postal operations . . . (Pub. L. 91-375, Aug. 12, 1970, 84 Stat. 719; Pub. L. 110-405, § 2(b)(9), Oct. 13, 2008, 122 Stat. 4289)
   b) Additionally, the delivery infrastructure should provide the recipients of said device, currently titled MAILABLE INSPECTOR COLLECTOR, to a genuine and true article and not a counterfeit. To accomplish that, the delivery infrastructure should have a policy similar to that of the United States Postal Service stating: Short Title of 2010 Amendment Pub L 111-155, § 1, Apr. 7, 2010, 124 Stat. 1112, provided that. "This Act [amending section 3001 of this title] may be cited as the 'Prevent Deceptive Census Look Alike Mailings Act'." and also
   c) Short Title of 2006 Amendment Pub. L. 109-435, § 1(a), Dec. 20, 2006, 120 Stat. 3198, provided that "This Act . . . may be cited as the 'Postal Accountability and Enhancement Act'." COVID-19 Borrowing Authority for the United States Postal Service Pub. L. 116-136, div. A, title VI, § 6001, Mar. 27, 2020, 134 Stat. 504, provided that: "(c)Prioritization of Delivery for Medical Purposes During COVID-19 Emergency.—Notwithstanding any other provision of law, during the COVID-19 emergency, the Postal Service—"(1)shall prioritize delivery of postal products for medical purposes; and "(2) may establish temporary delivery points, in such form and manner as the Postal Service determines necessary, to protect employees of the Postal Service and individuals receiving deliveries from the Postal Service."
   d) The aforementioned policy examples, adhered to by a delivery infrastructure, would accomplish the goal to provide the device titled MAILABLE INSPECTOR COLLECTOR, to the appropriate recipients for collecting bio-samples, analyzing results, and returning used elements to a facility for proper handling (e.g. for data analysis, recycling, disposal, etc.) while also being assured that the device titled MAILABLE INSPECTOR COLLECTOR, is the genuine working article.

FIELD OF THE INVENTION/TECHNICAL FIELD

This nanostructure invention, currently titled MAILABLE INSPECTOR COLLECTOR, in the present application, relates to a device intended for single-use detection of pathogens (e.g. virus-based particle, etc.), where test results are easily discernible.

CLASSIFICATION OF CLAIMS

Estimated classification of claims associated with device invention MAILALBE INSPECTOR COLLECTOR, (summarized):

Class 977 Nanotechnology/
- Sub-class 700 Nanostructure/
  - Sub-class 802 Virus-Based Particle/
    - Sub-class 806.: Subject matter wherein the exterior chemical attachment is adapted for a tracking purpose, e.g., used for recognizing the virus-based particle, etc./
    - Sub class 807: Exterior attachment for detection.

Alignment with the FDA

This invention was developed to address a current need to quickly and economically address the COVID-19 epidemic/pandemic. Additionally, this invention was created so that it could be adapted and modified for a future pathogenic outbreak. This device is considered a nanostructure device which is intended for submission to the United States Food and Drug Administration (FDA) for review (e.g. Investigational Device Exemption (IDE) as it relates to COVID-19).

FDA—Emergency Use Authorization (EUA):

The EUA is supported by the Secretary of Health and Human Service's declaration that circumstances exist to justify the emergency use of medical devices during the COVID-19 outbreak. The Secretary of HHS has declared that circumstances exist justifying the authorization of emergency use of in vitro diagnostics for the detection and/or diagnosis of COVID-19 (Feb. 4, 2020), personal respiratory protective devices (Mar. 2, 2020), and other medical devices, including alternative products used as medical devices (Mar. 24, 2020), for use during the COVID-19 outbreak pursuant to section 564 of the Act and subject to the terms of any authorization issued under that section. (Source: FDA Website: "Coronavirus Disease 2019 (COVID-19) Emergency Use Authorizations for Medical Devices") This invention titled MAILABLE INSPECTOR COLLECTOR would qualify for EUA pertaining to a device In Vitro Diagnostics EUAs for Individual EUAs for Molecular Diagnostic Tests for SARS-CoV-2.

FDA—EUA and Diagnositic Testing Kit Standards

The FDA recommends that a manufacturer intending to create and distribute a molecular SARS-CoV-2 diagnostic test kit using the EUA process, that the manufacturer use the "Molecular Diagnostics Template for Commercial Manufacturers" to help facilitate the preparation, submission, and authorization of an EUA and to contact CDRH-EUA-Templates@fda.hhs.gov. The FDA has also expressed a willingness to discuss an alternate approach. The FDA is interested in early interactions with COVID-19 testing manufacturers on a rolling basis, so there is no need to have all of validation and documentation completed and submitted in an EUA request to the FDA before engaging with the FDA. The FDA encourages manufacturers to begin pre-EUA discussions, even if the validation and/or documentation is not yet completed. The FDA can accommodate the best approach for completing validation, documentation, and submission of the EUA request. Contact the FDA at COVID19DX@fda.hhs.gov for a list of various test materials for assay validation supplies.

FDA—Impact to Healthcare Providers (HCP)

Healthcare Providers (HCP) would benefit from knowing that the device instructions for use are to include predictive screening in compliance with the Conditions of Authorization in the Letter of Authorization issued to the manufacturing organization by the FDA. This "predictive screening" is defined as generating a positive result with a small amount of the virus present in the test-subject, but before said subject evidences symptoms. This would include asymptomatic as well as pre-symptomatic Test Subjects. After collecting data, the compilation of data could deliver accurate predictive analytics useful for medical, ICU (Intensive Care Unit), tele-ICU personnel, and others interested in epidemiological elements, with information pertaining to trends. This data would better provide high-quality care to patients and allow HCPs to allocate appropriate resources to address the Coronavirus Disease 2019 (COVID-19) outbreak.

FDA—Viral Transport Media (VTM) Standards

A potential manufacturer should comply with FDA VTM regulations. Because this invention is new, the FDA has welcomed discussion pertaining to alternatives complying with standard regulations. The FDA is interested in interacting with commercial manufacturers of additional transport media device types, or that may wish to discuss alternative approaches to validation of VTM that are not identified in docket: FDA-2020-D-1138. This document shares that the FDA does not intend to object to the distribution and use of VTM (Viral Transport Media) by commercial manufacturers, without submission of a premarket notification to FDA as required by section 510(k) of the FD&C Act (21 U.S.C. 360(k)), or compliance with the Unique Device Identification (UDI) requirements in 21 CFR Part 830 and 21 CFR 801.20.

Otherwise, if the manufacturer intends to comply with standard VTM regulations, then the manufacturer is expected to include a statement that the transport medium has not been reviewed by the FDA and other appropriate labeling information. The FDA does not intend to enforce the Quality System Requirements under 21 CFR Part 820 when manufacturers conform to ISO 13485:2016 Medical Devices Quality Management Systems Requirements for Regulatory Purposes. Manufacturers should have documentation demonstrating their compliance with ISO 13485. It is recommended that any manufacturer familiarize themselves with guidelines prior to engaging in FDA discussions. The invention, in physical manufactured form, should ensure that transportation of any viral content would comply with the FDA regulations for transport media comprising of certain types of viral transport media (VTM) with the majority under 21 CFR 866.2390 and pertaining to Severe Acute Respiratory Syndrome Coronavirus 2 (SARS-CoV-2) assays or antigen-detection diagnostic SARS-CoV-2 assays for the duration of the COVID-19 public health emergency. Consult policy, docket number: FDA-2020-D-1138 titled, " . . . Nonbinding Recommendations Enforcement Policy for Viral Transport Media During the Coronavirus Disease 2019 (COVID9) Public Health Emergency". This is a guide for manufacturers who wish to develop viral transport media with molecular or antigen assays. This guide is intended to remain in effect only for the duration of the public health emergency related to COVID-19 declared by the Secretary of Health and Human Services (HHS) on Jan. 31, 2020, effective Jan. 27, 2020, including any renewals made by the HHS Secretary in accordance with section 319(a)(2) of the Public Health Service Act (PHS Act) (42 U.S.C. 247d(a)(2)).

Comments about docket number: FDA-2020-D-1138 can be addressed to Dockets Management, Food and Drug Administration, 5630 Fishers Lane, Rm 1061, Rockville, Md. 20852 CDRH-EUA-Templates@fdahhs.gov or 1-888-INFO-FDA. Some other organizations which have regulations pertaining to VTM include: Centers for Disease Control and Prevention (CDC), World Health Organization (WHO) Viral Transport Media, and Biosafety in Microbiological and Biomedical Laboratories (BMBL). It is recommended that the manufacturer will validate the VTM design prior to manufacture and distribution to ensure that the transport medium will preserve the viral particles without meaningful degradation which could lead to inaccurate test results. The goal of this invention is for a high level of testing accuracy. Manufacturers should consider consulting the document "Centers for Disease Control and Prevention& (CDC's) Standard Operating Procedure (SOP): Preparation of Viral Transport Media" before engaging in conversation with the FDA regarding alternative transport VTM types.

FDA Application: Investigational Device Exemption (Ide)

Before applying to for an IDE, the manufacturer should ensure sponsorship of the clinical trial needed for submitting the IDE is in order per FDA (§ 812.40). Likewise, the manufacturer should obtain Institutional Review Board (IRB) approval before the study can begin. Foreign companies wanting to conduct a clinical study in the U.S. MUST have a U.S. sponsor (§ 812.18). Under certain circumstances, the clinical investigator may wish to submit an IDE and would, therefore, also act as the sponsor of the study.

It is recommended the application for the FDA IDE is executed in this order: First, obtain IDE approval; Next, obtain study approval; Thirdly, enroll patients in the study at the appropriate study sites. Each site must have approval from the reviewing IRB for that site prior to beginning the study. Note that the review of applications by the FDA and the IRBs are independent and, therefore, may be submitted simultaneously. In some cases, it may be possible to apply to an early feasibility study (EFS), which is a limited clinical investigation with the goal of evaluating the design of the device with a limited number of subjects. Here, the manufacturer can modify the design before conducting a study with a large number of subjects. The Center for Devices and Radiological Health (CDRH)'s EFS Program facilitates the conduct of early feasibility studies in the United States to increase access for patients to potentially beneficial technologies and to support device innovation. EFS concepts are described in the FDA guidance document, "*Investigational Device Exemptions (IDEs) for Early Feasibility Medical Device Clinical studies, Including Certain First in Human (FIH) Studies*".

What Inspired the Invention Design?

The inspiration for the design of the MAILABLE INSPECTOR COLLECTOR came from the need to leverage both cutting-edge nanotechnology as well as low-tech methods of distribution, reading of test results, and test result interpretation.

To make a test easy for a subject to take, the test should be minimally invasive when collecting the bio-sample. From which location on the body does a the specific pathogen (e.g. Virus-based particle such as COVID-19) enter the body? Answer: The nose. If a bio-sample is to be contributed from the nose, the Test Subject must feel the process of contributing a specimen is minimally invasive. This means, the design needed to consider various sizes of nostrils from a varied demographic (or even varied species). The primary use of this invention MAILABLE INSPECTOR COLLECTOR is geared towards humans.

This device should accommodate a nose tip with nostrils which are wide. The mean area of the total nostril opening is 357.83 $mm^2$ (SD=108.09 $mm^2$. The largest nostril in the study had an area over 600 $mm^2$. (Source: Size of nostril opening as a measure of intranasal volume, Physiology & Behavior Volumes 110-111, 17 Feb. 2013, Pages 3-5 by V. A. Schriever, T. Hummel, J. N. Lundström, J. Freiherre).

Epithelial (skin) cells form the epithelium, or surface layer of the nasal mucosa, line the inside of nostrils and nose. This thin layer of skin serves as a physical barrier to infectious pathogens. Mucous in the nasal cavity is generated to remove foreign particles. If a pathogen invades this barrier of cells, the host can become infected. These epithelial cells work in the process whereby the pathogen is introduced to a T-lymphocyte cells (t-cells) which triggers an immune response. Similarly, they are involved in the process of triggering an allergic response.

This is one reason, that the bio-sample should be from the nose, as it appears to be a significant point of entry for a virus even before infection spreads to the rest of the host.

Another reason to select the nose from which to collect the bio-sample, is that the nose allows for a pathway for infection to the lungs. As explained earlier, the nostrils are tunnels which open into the choanae (or a singular choana) and then into a skin-lined chamber called the nasopharynx, the upper part of the throat (or the pharynx), connecting with the nasal cavity above the soft palate and then into the oropharynx, the throat area behind the mouth (between the soft palate and the hyoid bone). When air is inhaled through the nostrils, it travels through the nasal passages, the choanae, the nasopharynx, the oropharynx and the voice box and can end up in the lungs. This is the route used for infection of the lungs for respiratory pathogens. It is for this reason that a bio-sample from the nose is the most advantageous to detect infected hosts (Test Subjects) before they show symptoms. This includes pre-symptomatic and asymptomatic Test Subjects.

This invention shall allow for a host to provide a bio-sample for analysis even if that host does not evidence any other symptoms of infection. Therefore, an examination of diverse nose types is in order.

Noses can be categorized into three groups. Leptorrhine (narrow) and hyperleptorrhine (very narrow) describes a thin long and tall nose, which is commonly found in Caucasian races. Platyrrhine (wide) and hyperplatyrrhine (very wide) describes a wider flatter nose shape common with some African races. Mesorrhine (medium to medium-wide) is an intermediate nose which is common amongst Asian races. (Source: Garandawa Hi., Nwaorgu OGB, Oluwatosin OM. Nose parameters in adult Nigerians. BOMJ, 2005; 2(2):5-9).

For example, the smallest nasal index is found in the Inuit people originating from Arctic North America.

All three groups comprise different placement of nostrils pertaining to the human nose, the location of which is necessary for the deposit of bio-samples onto the SAMPLE COLLECTOR component of the device MAILABLE INSPECTOR COLLECTOR such that pathogenic analysis can commence. The bio-sample should be emitted from the two openings at the end of the nose called the anterior nares or two nostrils. The two nostrils lead to the nasal cavity which is lined with skin, and the primary entry point for the virus to incubate before spreading to the other areas of the body. However, instead of using an invasive swab, this invention presents a method which will utilize the subject's breathing as a way to guide potentially infected bio-samples from the nasal cavity onto the SAMPLE COLLECTOR of the device.

When a person inhales through the nose, air comes into contact with the moist mucosal surface of the nose. The process for this invention, the MAILABLE INSPECTOR COLLECTOR, is for a human test-subject to inhale through the mouth, position the SAMPLE COLLECTOR under the nostrils, and then exhale through the nose. If another breath is needed, the subject should once more inhale through the mouth and exhale through the nose to direct a bio-sample onto the SAMPLE COLLECTOR. This process can be repeated a few times to allow for adequate deposit of bio-sample content for analysis. Coronavirus can be detected with approximately 20 molecules of virus contained in the bio-sample. (Source: Journal of Virological Methods 193 (2013) 337-340, A new approach for diagnosis of bovine coronavirus).

Another benefit of this device is that it can be manufactured in a smaller size to accommodate smaller noses, such as those belonging to children. Likewise, it can be enlarged for use with larger livestock animals, such bovine dairy cows. Each cow nose is different. Extrapolating from cow nose prints which were taken by covering noses with common black ink, and then stamping the inked nose on a sheet of paper 8½ inches by 5 ½ inches, cow nostril placement shows nostril openings are approximately 2½ inches apart from each other. (Source: The Identification of the Bovine by Means of Nose-Prints by W. E. Petersen, Division of Dairy Husbandry, University of Minnesota, St. Paul, Minn., Journal of Dairy Science, Vol V, No. 3 OF Dairy Science, VOL, V, NO. 3 on Page 251).

The design laid forth in this invention, MAILABLE INSPECTOR COLLECTOR, shall assume the dimensions of a human nose as described earlier to design a user-friendly device which can be used by a diverse human population. This shall assume an average nostril diameter opening around 10 to 12 mm based on the average adult nostril opening area is 357.83 mm2 (source: Zhao K, Scherer P W, Hajiloo S A, Dalton P. Effect of anatomy on human nasal air flow and odorant transport patterns: implications for olfaction. Chem Senses 2004; 29(5):365-79)

HUMAN NOSE SHAPES SUMMARIZED:
  A. hyperleptorrhine (very narrow)
  B. leptorrhine (narrow)
  C. mesorrhine (medium-wide)
  D. platyrrhine (wide)
  E. hyperplatyrrhine (very wide)

The aforementioned information is simply to establish that dimensions of the device can be modified. Moving forward, however, an average human adult nose shall be assumed.

Usefulness of Invention

This invention is deemed useful as defined in 35 U.S.C. 101 because it addresses a current and imminent need to respond to a viral outbreak, which has resulted in a pandemic. This invention shall address specific needs, namely a mode of detection, tracking, sensing, analyzing, and/or identifying. This invention shall facilitate:
1. Easier distribution of pathogens (e.g. virus-based particles, etc) samples and test results.
2. Easier to distribute to general public (e.g. populations, communities, etc.) (mass distribution) by using existing delivery infrastructure
3. Easier sample collection for Test Subject to submit bio-sample
4. Enhanced ability to render rapid accurate results in a reasonable amount of time without complex laboratory equipment. Results can be interpreted easily after a few minutes.
5. Facilitate relevant data collection which could be used to analyze the spread of the pathogenic outbreak in a population (epidemiology), or for contact tracing, or other relevant data correlation, as well as to direct the used units to the appropriate data processing center and/or recycling center and/or disposal center to address used test components.

Additional benefits include: The manufacture of this unit would be cost-effective. Likewise, the cost to distribute this unit through existing delivery infrastructure, such as the United States Postal Service, would be approximately the cost of bulk-mail delivery charges. This device is considered "single-use", and has a disposal/recycling element built into it so that a process could support the appropriate disposal of the unit after results have been rendered. Likewise, the basic mechanism could me made larger or smaller to accommodate larger living subjects, such as livestock, or smaller living subjects, such as human children.

Additionally, the same elements can be adapted to object surfaces which may have been contaminated by the target pathogen. The information laid forth in this document addresses coronavirus specifically, however the MAILABLE INSPECTOR COLLECTOR can be adapted for other pathogen identification.

This single-use easy-to-read and easy-to-use MAILABLE INSPECTOR COLLECTOR not only can be used on a frequent basis, but it can also be disposed of properly by leveraging a delivery infrastructure, such as the United States Postal Service. Most components of the device could be bio-degradable, making it environmentally friendly. Given that a pathogen can also remain active on surfaces, this device can also be modified to collect samples from a surface and then be analyzed. Because the RETURNABLE MAILER is designed to be mailed after the test has been used, the mailer could also contain an optional installed artificial intelligence based data collection mechanism to collect data which would aid in analysis, or epidemiological data collection to facilitate contact tracing and community spread patterns. Additionally, the ANALYSIS PAD of the MAILABLE INSPECTOR COLLECTOR can be infused with the appropriate combination of chemicals to identify a specific pathogen, such as COVID-19.

Manner and Process of Making and Using Invention

Description of manner and process as per 35 U.S.C. 112(a) states that the device of invention shall be manufactured primarily for providing a low-cost easy-to-take and easy-to-interpret the results of a pathogen test which can be easily distributed and recycled. Alternative forms of the same mechanism can be manufactured in smaller dimensions to allow for a human child's nose, or larger to accommodate a farm animal, such as a dairy cow, which could be approximately 69 inches (1.8 m) tall and 103 inches (2.6 m) long, weighing up to 2,000 pounds (907 kg). This assumes an average head width of 30 inch (76 cm) wide, which would have a nose approximately 6 inches across the flat tip of the nose with nostrils spaced approximately 2½ inches apart. Because livestock may contribute bio-samples for pathogene analysis using this invention, MAILABLE INSPECTOR COLLECTOR, the invention was designed to be used in locations such as pastures which may not have access to electrical power, nor complex laboratory equipment.

Essential Materials are set forth in the section titled Detailed Description of the Invention. The explanation is full, clear, concise and exact as required by 35 U.S.C. 112(a). This invention resolves problems and the design of this invention demonstrates use to the general public, as required by 35 U.S.C. 112(b). Details pertaining to the process to use and dispose of a manufactured invention as well as the steps needed to assemble the invention is clearly stated to demonstrate that it can perform a specific function, as required by 35 U.S.C. 112(f). Background and references to source documents is listed as necessary throughout this document. Other Nonessential material needed to completely manufacture the device is listed in the appropriate section with clear reference to the documentation needed to consult. "Essential material" is defined in 37 CFR 1.57(d) Description of the structure, material, or acts which correspond to performing a specified function of collecting samples and analyzing those samples for the presences of specific targeted pathogens (e.g. virus-based particle, etc.) as required by 35 U.S.C. 112(f).

Elements Needed to Assemble Device Mailable Inspector Collector
  a) SAMPLE COLLECTOR—Element which collects the sample and is affixed to the TEST PLATFORM as part of the device, MAILABLE INSPECTOR COLLECTOR
  b) ANALYSIS PAD—Element which makes contact with the SAMPLE COLLECTOR to commence analysis of collected sample. The ANALYSIS PAD is affixed to the TEST PLATFORM as part of the device, MAILABLE INSPECTOR COLLECTOR
  c) PROTECTIVE TRANSPARENT VIEWER—Element used to cover and/or to protect sample and analysis components while allowing the user to see through this viewer to ascertain if there is a change of state (e.g. color-change, fluorescence, etc.) of the elements being analyzed. The PROTECTIVE TRANSPARTENT VIEWER is affixed to the TEST PLATFORM as part of the device, MAILABLE INSPECTOR COLLECTOR
     Note: The PROTECTIVE TRANSPARENT VIEWER and ANALYSIS PAD, and the SAMPLE COLLECTOR all reside on the TESTING PLATFORM and can be collectively referenced as the lab.
  d) RETURNABLE MAILER—Element used to send device, MAILABLE INSPECTOR COLLECTOR, to a specific address and then return that device in the same mailer to an appropriate facility (e.g. Data Processing Center, Recycling Center, Disposal Center, etc.)
  e) TEST PLATFORM—This is a sub-component of the device, MAILABLE INSPECTOR COLLECTOR, which serves as a dedicated area to which the other testing elements are affixed. Generally, this sub-component would be enclosed inside, or attached to, the RETURNABLE MAILER during dispatch, when the RETURNABLE MAILER is en route via the selected delivery infrastructure (e.g. United States Postal Service).

Making the MAILABLE INSPECTOR COLLECTOR

Terms Used in This Section a. (PAN) electrospun polyacrylonitrile nanofibrous scaffold
b. (PET) melt-blown polyethylene terephthalate
c. (UFCNs) ultra-fine cellulose nanofibers which form an interwoven membrane nanostructure network
d. (m-UFCNs) modified or diamine-modified ultra-fine cellulose nanofibers which can be electrostatically charged to attract a virus
e. (MCCNs) microcrystalline cellulose nanofibers which can wrap around the electrospun scaffolding nanofiber without forming networks, which could be used to sieve for larger bacteria, if needed.
f. Portable isothermal assay is used for the detection of pathogens without complex laboratory equipment.
g. (RT) When this term is used with another term, it means "real time" or a way of processing in a more rapid fashion than is currently accepted as an acceptable standard processing duration.

The electrostatic charge is obtained on the membranes with an infusion of the cellulose nanofibers. (MCCNs followed with modification of a positively charged polymer and m-UPCNs into the electrospun PAN layer of the PET support. The nanofibers help to adsorb viruses by charging through pH values. For example, using a Bacteriophage MS2 virus, approximately 30 nm in size, the isoelectric point of that Bacteriophage MS2 virus is 3.9 at a pH of 7.

Since most viruses tend to be slightly negatively charged, the electrostatic interactions between a positively charged nanofiber surface and the slightly negatively charged virus is attractive and adsorption does take place to lock the virus to the surface of the nano-fibrous nanostructure. The small (less than 1%) amount of cellulose infused into the nanofiber membrane, resulted in the adsorption effect which is still prominent because the total surface area of the ultra-fine nanofibers is large by comparison. Electrostatic charging works better at securing the virus than any sort of physical sieving. In other words, a virus of 30 nm in size was trapped and held in the electrospun PAN scaffold infused with the m-UFCNs. The microfibers are entangled with the infused m-UFCNs. These cellulose nanofibers also create a network that is supported by the scaffold with various pore sizes ranging from tens to hundreds of nanometers. In the example in the white paper, the diameter of the m-UFCN is about 5-10 nm. The marked x-y-direction is parallel to the membrane surface, while the z-direction is perpendicular to it. The sample was slightly coated with carbon to minimize charging during observation. The m-UFCN (diamine-modified UFCNs) network formed along the direction of the membrane normal. (Source: Journal of Electron Microscopy 60(3): 201-209 (2011) Novel nanofibrous scaffolds for water filtration with bacteria and virus removal capability doi: 10.1093/jmicro/dfr01).

The conronavirus is predominantly negatively charged, leaving a negatively charged residue. One research paper suggests the coronavirus is more negatively charged than positively charged: " . . . negatively charged Endo residues for the incorporation of MHV S protein into assembled virions. . . . Additionally, the heptapeptide TENLNNL, created by two of the reverting mutations, introduced one negatively-charged glutamic acid (E) plus four polar residues (T and N) that might be beneficial to the assembly of S . . . this S-interacting surface must have one or more key positively-charged residues that contact the negatively-charged charge-rich motif of the MHV S Endo." (Source: Virology. 2013 Jul. 20; 442(1): 74-81. doi: 10.1016j.virol.2013.04.001 Negatively charged residues in the endodomain are critical for specific assembly of spike protein into murine coronavirus). This demonstrates that the coronavirus is predominantly negatively charged and could be contained by a positively charged nanostructure.

Making the SAMPLE COLLECTOR

SAMPLE COLLECTOR: This is comprised of a nanofiber mesh. The purpose of this mesh is to capture deposited bio-sample (nasal exhale). This is a sample collected when a Test Subject exhales through the nose with force generated from Test Subject's diaphragm contraction. The fiber has a positive electrostatic charge to attract the negatively charged virus, which then traps or adsorbs the virus to the surface of the positively electrostatically charged fibers similar to the manner in which a magnet attracts its polar opposite. The pore size of the nanofiber mesh can be modified to accommodate the pathogen size to be trapped.

Making the ANALYSIS PAD

ANALYSIS PAD. This pad will touch the surface of the SAMPLE COLLECTOR, which collects and traps the bio-sample which could contain elements of a pathogen. The ANALYSIS PAD is attached to the TEST PLATFORM, which is a sub component of the device MAILABLE INSPECTOR COLLECTOR. The ANALYSIS PAD is infused with chemicals to develop and/or sense the presence of a pathogen and render results. This ANALYSIS PAD will contain an infusion of enzymes, and/or primers, and/or excipients, and/or probes. To specifically identify a coronavirus, this pad (such as a nano-membrane material) should contain elements to identify a minimum viral sample size of approximately 21 molecules.

a. RT-Portable isothermal primers
b. RT-Portable isothermal exo probe
c. Reverse Transcriptor
d. RNase inhibitor
e. DTT (Dithiothreitol (DTT)
f. Acetate
g. Buffer used on the sample to denature and solubilize bio samples
h. RNA template—the more template, the more pronounced the visual result
i. dry enzyme Should fluorescence be used, it could be measured in the FAM channel (Excitation 470 nm, Detection 520 nm, 42° C. for 20 min).

Note: In process of creating a specific analysis for a strain of coronavirus, a forward and reverse primer should be created for that specific mutation of the target pathogen (e.g. virus-based particle, etc). As an example:

The RT-Portable isothermal forward primer
5'-GCTATAATGGTGCAATTAGATTTGACAGT-3',
RT-Portable isothermal reverse primer
5'-GCTGACGCTGTGGTTTGGACTCATATTC-3'
for the detection of coronavirus N gene were designed using GenBank sequences (EF193073-EF193074). The Portable isothermal assay amplicon was placed between nt 30451 and 30585 of the GenBank accession number U00735 (length 135 nt). The Portable isothermal exo probe was synthesized as following 5'-GGACTCATATTCATCATAC-CATCTTGTTGT (BHQ1-dT) (THF) (FAM-dT) ATGC ATTCAAATTCTC-Phosphate. (Source: Journal of Virological Methods 193 (2013) 337-340, A new approach for diagnosis of bovine coronavirus).

When considering targeting an element of a virus, for example a Spike Protein (s), and revealing it by use of fluorescence, note that studies have been conducted (SOURCE:DOI: 10.1128/JVI.79.11.7195-7206.2005, Identification and Characterization of the Putative Fusion Peptide of the Severe Acute Respiratory Syndrome-Associated Coronavirus Spike Protein.) which noted "Fluorescence was recorded at excitation and emission wavelengths of 280 and 340 nm, respectively, and with 8-nm bandwidths by use of an SML Aminco 8100 spectrofluoromete.... Measurements were carried out in 5 mM HEPES, 100 mM NaCl, pH 7.4. Peptides were added from stock solutions in DMSO to 250 l of buffer and mixed by inversion." This means that a target pathogen, which includes but is not limited to a virus-based particle, bacteria-based particle, or fungi-based particle, should be identified by size and/or potential fluorescence. This includes noting at what temperature the fluorescence is detected, and what pH level the fluorescence is detected before manufacturing the ANALYSIS PAD for that specific pathogenic target. In other words, measure the emission (single or double) peak (e.g. 340 nm) resulting from an excitation source (e.g. UV light source of 280 nm) to ascertain the cellular fluorescence signal range for detection of pathogen (e.g. bacterial, etc.) target.

Making the TEST PLATFORM

TEST PLATFORM—This is a sub-component of the device. The purpose of this platform is to secure the testing elements. One element, the ANALYSIS PAD, is affixed securely to the TEST PLATFORM. The other two elements pivot or rotate with a mechanism on top of the ANALYSIS PAD in such a manner that the sample collected in the SAMPLE COLLECTOR element can be face-up to receive a freshly deposited sample from a test-subject, and then pivot in a hinged manner to be positioned face down on top of the ANALYSIS PAD. This TEST PLATFORM should be able to allow for the attachment of at least one mechanism which would allow the SAMPLE COLLECTOR to execute such an action. Likewise, at least one similar pivoting hinge-like mechanism will need to secure the PROTECTIVE TRANSPARENT VIEWER to the TEST PLATFORM. The entire platform is then itself, in its entirety rotated around to the reverse side of the RETURNABLE MAILER before the RETURNABLE MAILER is packaged to be returned to an appropriate destination using a delivery infrastructure (e.g. United States Postal Service, etc.).

Making the PROTECTIVE TRANSPARTENT VIEWER

PROTECTIVE TRANSPARTENT VIEWER. This layer serves to seal in the bio-sample with the analysis components. Once this protective coating is in place, locking in the SAMPLE COLLECTOR and the ANALYSIS PAD, the elements are able to marinate until a visible result reveals itself. At this point, the sealed bio-sample and analysis elements can be warmed to a minimum of 98.6° F./37° C. The temperature does not need to exceed 107.6° F./42° C. Because the sample is now sealed, the flat components can be held flat in the palms of the hand to ensure the temperature is held at 98.6° F./37° C. as results develop in approximately 20 minutes. This demonstrates that the warming can be accomplished without complex laboratory equipment. The PROTECTIVE TRANSPARTENT VIEWER is folded over on top of the two other components, the ANALYSIS PAD covered by the SAMPLE COLLECTOR and then the PROTECTIVE TRANSPARENT VIEWER on top. The manufacturer of this component may optionally coat the underside of this PROTECTIVE TRANSPARTENT VIEWER with a buffer (after the SAMPLE COLLECTOR and ANALYSIS PAD have rendered test results in the appropriate duration of time). The higher the viral load in the bio-sample, the sooner results could reveal themselves. It is reasonable to assume that positive results could present themselves, for example, after 3 minutes. This layer is translucent so that the color-change or fluorescence can be discerned easily. Once the allotted time has passed, a buffering agent may be added to stabilize the pH levels of the bio-sample and analysis elements. Should a buffering agent be added at the end of the processing time, the user should confirm the transparent seal is affixed properly. If results are positive (pathogen is present) then there will be a color change. If the results are negative (no pathogen is present in the bio-sample) there will not be a color change.

a) The aforementioned section(s) referenced:
(Source: Lab on a Chip. 2012 Sep. 7; 12(17): 3082-3088. doi:10.1039/c21c40423k).
(Source: Journal of Virological Methods 193 (2013) 337-340, A new approach for diagnosis of bovine coronavirus).
(Source: Virology. 2013 Jul. 20; 442(1): 74-81. doi: 10.1016/j.virol.2013.04.001 Negatively charged residues in the endodomain are critical for specific assembly of spike protein into murine coronavirus.)

Making the RETURNABLE MAILER

RETURNABLE MAILER. Once the bio-sample has been processed and pathogen presence has been discerned, the sample can be disposed of. The best way to do this is to take the sealed sample secured by the PROTECTIVE TRANSPARENT VIEWER seal, which is affixed to the TEST PLATFORM and fold it into the accompanying mailer to be sent back via the United States Postal Service or other appropriate delivery system to the appropriate recycling, disposal, or data analysis center. The mailer itself should be manufactured in compliance with United States Postal Service guidelines for mailers, the minimum size of which measures approximately 3½ inches by 5 inches by ⅛th inch thickness in accordance with United States Postal Service stipulation Machinable Letters and Cards (201.1.0) for envelop sizes which can be sorted by machine. USPO Quick Service Guide section 201 addresses Physical Standards for Commercial Letters and Postcards. Section 3.1 addresses folded self-mailer booklet or postcards to comply with United States Postal Service regulations. A "folded mailer" is defined in US Postal section 3.14 Folded Self-Mailers.

When constructing the RETURNABLE MAILER, the manufacturer should consider making the device in compliance with the USPS Untied States Domestic Mail Manual, in particular, the following sections:

200 Commercial Letters, Flats, and Parcels Design Standards
   201 Physical Standards
      1.0 Physical Standards for Machinable Letters and Cards
      3.0 Physical Standards for Machinable and Automation Letters and Cards
      3.14 Folded Self-Mailers
      3.15 Other Unenveloped Mailpieces
      3.17 Postcard As described, this invention MAILABLE INSPECTOR COLLECTOR will be useful in collecting and identifying the presence of a pathogen, for example, the virus COVID-19. This invention will be useful because it presents a low-cost means of manufacturing and a low-cost means of distribution to a large population. Likewise, this device contains a process whereby the proper disposal of the used test can be executed to minimize waste and litter and be ecologically responsible. This device will detect a pathogenic infection of a submitted sample. This invention will allow for more regular testing. The invention can be produced in different sizes to accommodate average sized human adults, human children, small animal hosts, large livestock hosts, as well as collecting samples on inanimate object surfaces.

This device has shown that it meets a public need to have a test which demonstrates:
1. Easier to distribute/administer to the general public (e.g. populations, communities, etc.) (mass distribution) by using existing delivery infrastructure
2. Easy for the Test Subject to use. Can be made in various sizes.
3. Able to render rapid accurate results in a reasonable amount of time without complex laboratory equipment. Results can be interpreted easily after a few minutes.
4. Facilitate data collection of relevant data which could be used to analyze the spread of the pathogenic outbreak in a population (epidemiology), or for contact tracing, or other relevant data correlation . . . as well as direct the used units to the appropriate data collection center and/or recycling center and/or disposal center to process used test components.

High Level Process for Use:
1. Manufacture- ->2. Distribution- ->3. Receive Test- ->4. Taking Test- ->5. Process Test- ->6. Read Test Results- ->7. Contact Tracing & Data processing- ->8. Dispose of Test Detailed Process for Use:
1. Manufacture
   a) Manufacturer shall assemble the device.
   b) Instructions for component assembly are explained elsewhere in this document.
2. Distribution
   a) Manufacturer shall distribute the device via an established distribution delivery system, such as the United States Postal Service, for example.
   b) Considerations for delivery infrastructure selected for distribution: There are two legs which are delivered: Leg 1 is from the manufacturer to the Test Subject. Leg 2 is from the Test Subject to deliver the used test to a processing center. It is suggested that a separate dedicated drop box be utilized for the used test on Leg 2. The destination address of Leg 2 would be delivery to data collection, recycling, and/or disposal of the used test device. There should be a system of dedicated drop-boxes to expedite delivery for both Leg 1 and/or Leg 2. A dedicated box is to lower the risk of contamination or contagion.
3. Receive Test
   a) Individual Test Subject can receive a single unit delivered to a specific address.
   b) Organizations, such as hospitals or corporations, can receive large quantities of these units bundled into an easy to distribute larger bulk-package. Once the organization has accepted the bundled package, it is able to distribute single-use units to Test Subject directly. These larger bundled units can also be delivered to a specific address.
   c) Field or rural organizations which may at times be without access to sophisticated laboratory equipment and/or basic power, can also take this test. Test Subjects may include humans and/or animals and/or objects.
4. Taking Test
   a) Making the test easy-to-take (user-friendly) addresses the problem of ease of use, as set forth earlier in the Background of the Invention.
   b) The Test Subject shall open the sealed device to expose the TEST PLATFORM, which contains the testing elements (SAMPLE COLLECTOR, ANALYSIS PAD, and PROTECTIVE TRANSPARENT VIEWER).
   c) The Test Subject shall contribute a bio-sample to the SAMPLE COLLECTOR of the device.
   d) The SAMPLE COLLECTOR, which now holds the contributed sample, should be large enough for most nostrils to contribute a sample from at least one nostril.
   e) The individual Test Subject, or a trained assistant, can aid the Test Subject in folding over the contributed sample from SAMPLE COLLECTOR onto the ANALYSIS PAD. The elements infused in the ANALYSIS PAD can be modified to analyze and detect other pathogens besides COVID-19.
   f) The elements are left to process in order to determine if there is a pathogen present in the sample. The elements are covered by the PROTECTIVE TRANSPARENT VIEWER, which will allow the results to be viewed easily.
   g) Should a larger version of this test be used on livestock, then the Test Subject would require human/robotic/mechanical assistance to properly submit bio-sample and process the test.
   h) Should a smaller version of this test be used on small living Test Subjects, such as children, then a human assistant would be required to render assistance to the small Test Subject.
   i) Should the Test Subject be an object and not a living Test Subject, then the assistance of a human (or robotic/mechanical aid or assistant) would be needed to collect the sample from the object.
   j) Should the collection of a sample which may contain a pathogen be collected in another manner not laid forth in this document, then assistance may be rendered by (either a trained robotic device or) a trained adult human assistant to ensure the sample is collected and processed appropriately.
5. Process Test
   a) Processing the test to ensure clear and accurate results in an easy manner without complex lab equipment also addresses the problem of easy-to-discern test results, as set forth earlier in the Background of the Invention.
   b) The bio-sample is processed, at a minimum heat level of 98.6° F./37° C. which is human body temperature, so there is no need for sophisticated laboratory equipment.
6. Read Test Results
   a) The ability to read the test results without complex lab equipment also addresses the problem of clearly determining if a pathogen is present, as set forth earlier in the Background of the Invention.
   b) Results shall be easily apparent visually without complex laboratory equipment. If positive, there will be a color change indicating the presence of a pathogen. If negative, there will be no color change, confirming no pathogen is present. Additionally, florescence may be used.
7. Contact Tracing & Data Processing
   a) By leveraging an established delivery infrastructure service, such as the United States Postal Service or a similar nation-wide delivery infrastructure, the fold-over mailer configuration will allow for the device unit to be delivered to a specific address. Additionally, the same unit is designed to fold over and reveal a "return to" address whereby the original unit, the used test elements, and the original address to whom the unit was delivered, can also be returned.
   b) There is sufficient room on the fold over mailer for a manufacturer to embed a chip and/or other element to allow for geographic tracking, or to operate in some other capacity to further the tracking and/or analysis of a particular pathogenic outbreak for pandemics or epidemics, and/or other data collection needs.
  c) There is sufficient room on the fold over RETURNABLE MAILER for a manufacturer to place a printed code which can be interpreted by a scanner-type-interpretation-mechanism to read or interpret information such as medical data regarding the recipient of the MAILABLE INSPECTOR COLLECTOR device and correlate that to a positive or negative test result.
  d) There is sufficient room on the fold over RETURNABLE MAILER for the manufacturer to place a questionnaire or survey for the recipient test-taker, or their qualified trained assistant, to complete. This space may also be used for instructions or other relevant information in any language for the recipient Test Subject to follow.
8. Dispose of Used Test
  a) Test disposal can leverage the same distribution process, which is a problem addressed earlier in the Background of the Invention.
  b) The unit is disposed of in the same manner in which it was received, through the United States Postal Service, or similar distribution infrastructure. This MAILABLE INSPECTOR COLLECTOR device is designed to use existing infrastructure to distribute and get the used exhausted test back to a data collection and/or disposal and/or recycling center. This will eliminate needless waste and litter. This will enforce ecological responsibility.
  c) There is sufficient room on the fold over RETURNABLE MAILER for the manufacturer to print a TO: Recipient address (LEG 1) as well as a RETURN TO: secondary address (LEG 2) to which the Test Subject may send back the used components of the MAILABLE INSPECTOR COLLECTOR device by re-configuring (re-folding) it into a delivery-ready LEG 2 configuration.

The author of this document, Gretchen Jolie dePillis, is also the inventor, and the filing of this application takes place in the year 2020, which is after Sep. 16, 2012. The aforementioned content demonstrates specific and substantial utility and a benefit to the general public. Thus, this section pertaining to the Background of the Invention has concluded.

BRIEF SUMMARY OF THE INVENTION

The purpose of this brief summary of the invention is to apprise and inform the public and any potential manufacturers of the exact nature, operation, and purpose of this invention in a summarized form. The general statement of the invention, as set forth in 37 CFR 1.73. This invention resolves known problems and the design of this invention demonstrates use to the general public, as required by 35 U.S.C. 112(b).

This invention, Mailable Inspector Collector, relates to a single-use user-friendly (e.g. easy for a Test Subject to contribute a bio-sample, etc.) device which can be distributed and collected via an established delivery infrastructure system, such as the United States Postal Services (e.g. mass distribution to the public), for the purposes of sample collection, rapid accurate sample inspection, relevant data analysis (e.g. contact tracing, test results, etc.), and discerning rendered test results which will be visible for the purposes of determining pathogenic presence without complex laboratory equipment. This Mailable Inspector Collector should be a device which is low-cost to make, low-cost to take, low-cost to convey, for all our sakes.

BRIEF DESCRIPTION OF THE SEVERAL VIEWS OF THE DRAWING(S)

In accordance with MPEP § 608.01(f). A reference to and brief description of the drawing(s) as set forth in 37 CFR 1.74, This section shall list a brief description listed by figure number. This invention is a recyclable pathogen test packaged in a novel dual-purpose envelope which can be delivered via a delivery infrastructure. The test initiates by collecting the sample via exhaling air through the nostrils onto a nano-structure (106) to contain the bio-sample. Then, folding elements will immediately begin to analyze the collected sample to ascertain the presence of a pathogen. After use, the same envelop is refolded to send contents to a second address for processing (data collection, recycling of components, and/or disposal). This device is designed to minimize waste, use eco-friendly elements, and leverage an existing delivery infrastructure with a mail-worthy mailpiece which can be used twice (once for sending the fresh unused device to a Test Subject and once to deliver the used device to the processing center). This invention provides an economical test for pathogens which is easy to take, easy to quickly analyze to determine the presence or absence of a pathogen, as well as an easy mechanism to mass-distribute this test while also allowing for a vehicle to better effect contact tracing The detailed description of each figure shall be in the Detailed Description of the Invention section.

FIG. 1 Front flat view of unfolded device.
(Details in Paragraph 0091)
FIG. 2 Back flat view of unfolded device.
(Details in Paragraph 0102)
FIG. 3 Front flat view Manufacturer folding for Leg 1 Lab Visible.
(Details in Paragraph 105)
FIG. 4 Perspective of fold in progress for Leg 1
(Details in Paragraph 0107)
FIG. 5 Front flat view of folded device not yet sealed for Leg 1 (Continuation of FIG. 3)
(Details in Paragraph 0109)
FIG. 6 Back flat view of folded device not yet sealed for Leg 1 (Reverse of FIG. 5)
(Details in Paragraph 0111)
FIG. 7 Front flat view of folded and sealed device for Leg 1 (Continuation of FIG. 5)
(Details in Paragraph 0113)
FIG. 8 Back flat view of folded sealed device for Leg 1 where TO:address is visible and device is ready to be mailed—END of Leg 1 preparation (Continuation of FIG. 6. Reverse of FIG. 7)
(Details in Paragraph 0115)
FIG. 9 Test Subject opens three sides of device
(Details in Paragraph 0117)
FIG. 10 Perspective view of opened device to reveal test platform
(Details in Paragraph 0119)
FIG. 11 Perspective of device being used by Test Subject (nose placement indicated)
(Details in Paragraph 0121)
FIG. 12 Perspective exploded view of folding test platform for start of Leg 2
(Details in Paragraph 0123)
FIG. 13 Exploded flat view for Leg 2—First fold
(Details in Paragraph 0129)

FIG. 14 Exploded flat view for Leg 2—Second fold
(Details in Paragraph 0131)

FIG. 15 Front view test platform fold for Leg 2 (Continuation of FIG. 14)
(Details in Paragraph 0133)

FIG. 16 Back view for Leg 2 (Reverse of FIG. 15)
(Details in Paragraph 0135)

FIG. 17 Front flat folded view for Leg 2 (Continuation of FIG. 15)
(Details in Paragraph 0137)

FIG. 18 Back flat folded view for Leg 2 (Reverse of FIG 17)
(Details in Paragraph 0139)

Figure 19:
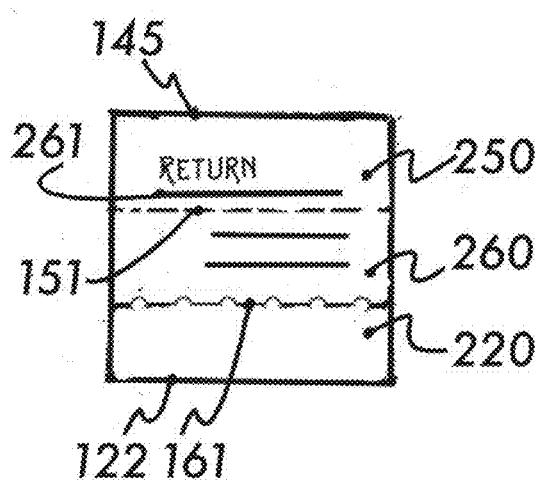

FIG. 19 Front flat fully folded for Leg 2—Return address visible (Continuation of FIG. 17)
(Details in Paragraph 0141)

Figure 20:
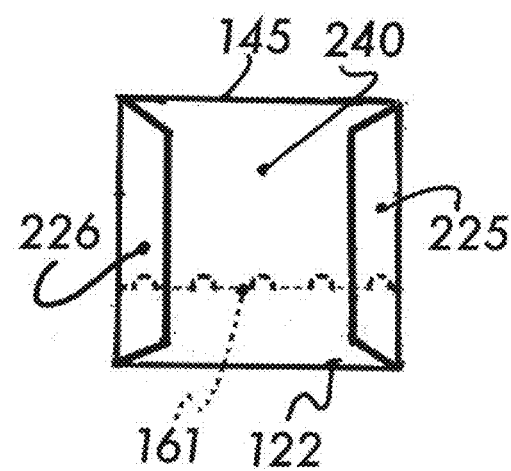

FIG. 20 Back flat fully folded for Leg 2 Sealed tabs visible (Reverse of FIG. 19)
(Details in Paragraph 0144)

Figure 21:
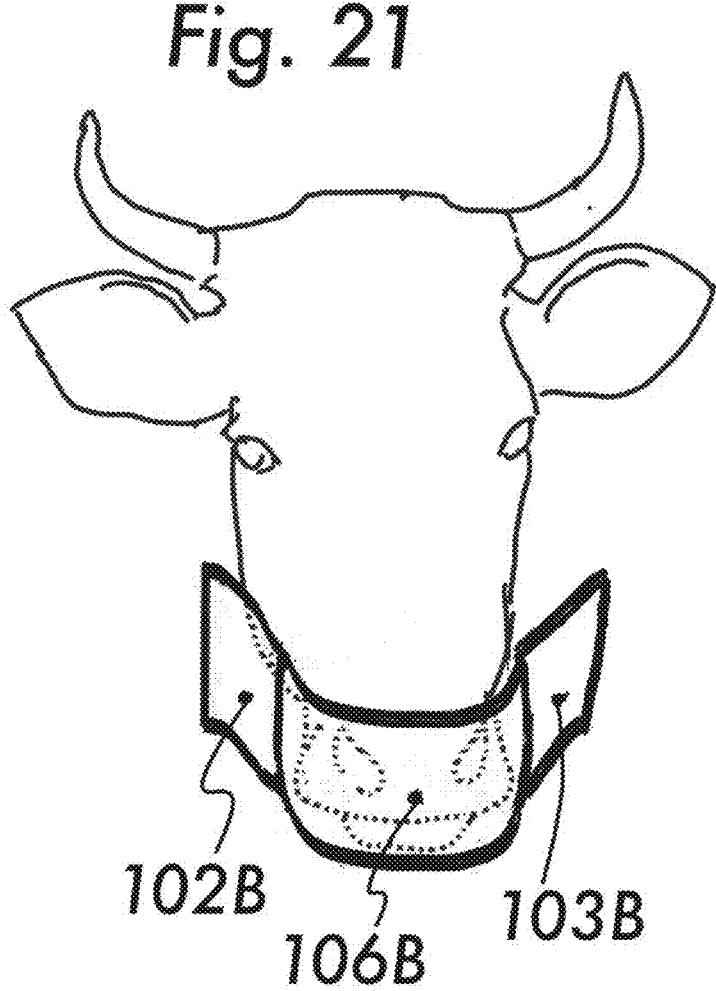

FIG. 21 Detached SAMPLE COLLECTOR in larger size for livestock use
(Details in Paragraph 0146)

END of Brief Description of the Several Views of the Drawing(s)

DETAILED DESCRIPTION OF THE INVENTION

The detailed description of this invention shall specify how the main problems set forth in the Background of the Invention, are resolved because this invention will address: Easier mass distribution to the public, easy to implement, rapid accurate results, and contact tracing. This section shall reference each figure number, drawing title, and detailed description. The device, MAILABLE INSPECTOR COLLECTOR, may be referred to as MIC in this section for brevity. This section is intended to show how the elements, when assembled, resolve the issues set forth in Background of the Invention in a cost effective manner, with a distribution and collection method utilizing an existing distribution infrastructure, such as the United States Postal Service, for example. This section, as well as the BACKGROUND of The INVENTION section shall support the concept this device, MIC, is a "well-defined and particular benefit to the public." as per In r Fisher, 421 F.3d 1365, 1371, 76 USPQ2d 1225, 1230 (Fed. Cir. 2005)

Detailed Description of Elements of the Invention

DEFINITION: Leg 1 is defined as manufacturer preparation to mail the fresh unused device to a Test Subject or other specific address; then Test Subject will use the MIC device. Then Leg 2 is defined as Test Subject preparation to mail the used MIC device to a processing address. Mailable Inspector Collector is abbreviated as MIC. The term lab refers to all the elements required for collection of a bio-sample, testing, and analysis, all of which are affixed to the TEST PLATFORM (100).

FIG. 1 Front flat view of unfolded device.

This drawing of the invention shows the full unfolded flat front of the MAILABLE INSPECTOR COLLECTOR. Each panel is separated by the foldable horizontal crease/axis as indicated by dashed lines. The entire TEST PLATFORM (100) is located at the bottom (or the south position). Starting from the bottom the element which looks like window is the PROTECTIVE TRANSPARENT VIEWER. This is comprised of a frame (108) and the transparent window-pane (109). This is attached to TEST PLATFORM (100) by a hinge (110), located to the north or top end of the PROTECTIVE TRANSPARENT VIEWER (110, 109, 108). Moving up, the ANALYSIS PAD (101) is a sponge-like nano-structure which is infused with the chemicals needed to conduct an inspection of the bio-sample. The ANALYSIS PAD (101) is affixed firmly to the TEST PLATFORM (100) and does not move. It shall serve as the "bottom layer" after other components have folded on top of the ANALYSIS PAD (101), which will be further explained in other figures. To the north (or above) the ANALYSIS PAD (101) is a SAMPLE COLLECTOR, comprised of parts handle (103), hinge (105), nano-pad (106), hinge (104), handle (102), horizontal hinge (107). This SAMPLE COLLECTOR is the place where a Test Subject places their nostrils (on part 106) to deposit a bio-sample to be analyzed. The bio-sample is collected by leveraging the Test Subjects strong diaphragm-based breathing to propel an exhale though the nostrils so the bio-sample lands onto the nano-structure (106) of the SAMPLE COLLECTOR.

This SAMPLE COLLECTOR is, in effect, the landing strip for any potential pathogens. This nano-structure nano-pad (106) of the SAMPLE COLLECTOR and is constructed in a fashion whereby wells or depressions are engineered to be the appropriate size to attract electrostatically the virus-based particle (which is emitted through the nostrils). The fiber has a positive electrostatic charge to attract the negatively charged virus, which then traps or adsorbs the virus to the surface of the positively electrostatically charged fibers similar to the manner in which a magnet attracts its polar opposite. The wells are constructed to allow a virus-based particle to adsorb to the surface of the nano-fiber which comprises the nano-structure nano-pad) electrostatically and remain secured in the appropriately sized wells electrostatically in preparation to immediately pivot over a hinge-like (107) element to come into contact with the ANALYSIS PAD (101), also described.

The SAMPLE COLLECTOR Nano-structure (106) is constructed of membrane-scaffolding of the appropriate pore or well depression size for target pathogen. As an example: Cellulose network modified with a positively charged polymer to adsorb a negatively-charged virus-based particle (for example, a coronavirus based particle, etc.) to the surface by charging through pH values to find the optimal iso-electric point of a target pathogen in the appropriate pH with the end result being to lock the virus-based particle to the surface of the nanostructure through the full course of analysis.

Figure 12:
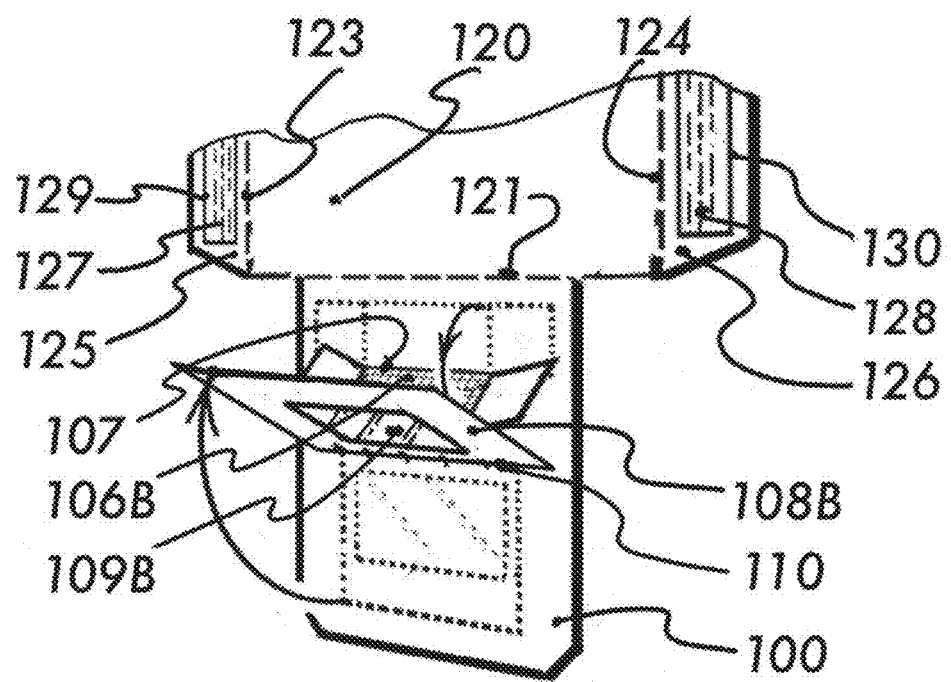

The ANALYSIS PAD (101) is also a nano-structure. This part 101 is fashioned in sponge-like honey-comb manner, which can contain the chemicals needed for analysis of a specific pathogen. The surface will come into contact with the pad of the SAMPLE COLLECTOR (106) and after a duration of time (approximately 3 to 20 minutes, depending on the target pathogen) will present the evidence or absence of the target pathogen through the underpart of part (106) by showing a color change or fluorescence visible via part (106B) as seen in FIG. 12. This ANALYSIS PAD (101) will contain an infusion of enzymes, probes, and primers (isothermal forward and reverse). Both nano structures (ANALYSIS PAD (101) and SAMPLE COLLECTOR nano-pad (106)) are manufactured to support real time portable isothermal assay methodology which would present results to the user in a visible color change or fluorescence if target pathogen is present, depending on the target pathogen selected.

Figure 11:
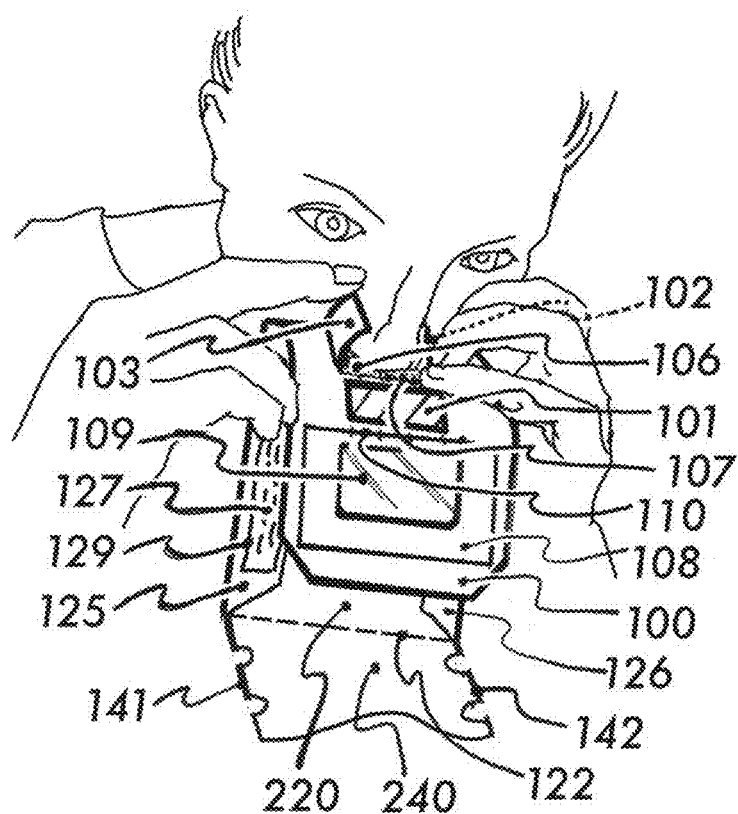

The SAMPLE COLLECTOR handles (103, 102) are constructed from a flexible material which pivot upward along vertical hinges (105, 104). This is to create a secure fit around the Test Subject nostrils which are placed on part (106), as illustrated in FIG. 11. After Test Subject has deposited a nasal bio-sample, the entire SAMPLE COLLECTOR pivots via hinge (107) downward. This is so it aligns the collected elements trapped in part (106) on top of the ANALYSIS PAD (101). All of these components can be referred to as the "lab". In other words, the "lab" affixed to the TEST PLATFORM (100) is comprised of: PROTECTIVE TRANSPARENT VIEWER (window frame 108, window 109, horizontal hinge 110), ANALYSIS PAD (101), SAMPLE COLLECTOR (handle 102, handle 103, vertical hinge 104, vertical hinge 105, nano-pad 106, horizontal hinge 107).

The exposed adhesives will be used by the manufacturer to fold the device for Leg 1 delivery. FIG. 1 illustrates covered adhesives (adhesive 127 covered by 129; adhesive 128 covered by 130; and adhesive 162 covered by 163). The Test Subject will remove these coverings after they have conducted the test to fold the RETURNABLE MAILER stock material component of the MAILABLE INSPECTOR COLLECTOR device for mailing on Leg 2 delivery.

Still on FIG. 1, the next panel north of crease (121) which is north of TEST PLATFORM (100), is crease (121) as indicated by a horizontal dashed line. This crease is on the south end of the panel (120). To the north or top of this panel (120) is another horizontal crease (122) as indicated by dashed horizontal lines. On the west side of this panel (120) is another vertical crease (123) which attaches to a tab (125). This tab is intended to be used on Leg 2 by the Test Subject so this tab (125) has both an adhesive strip (127) and a protective cover to that adhesive strip (129) where the underside of the west tab cover (129) is a material which will retain the integrity of the adhesive stickiness until the cover is removed. On the east side of this panel (120) is another vertical crease (124) which is connected to the east tab (126). As with the west tab (125), this east tab (126) has both an adhesive strip (128) and a cover for the adhesive strip (130), as this east tab (126) is intended to be used by the Test Subject for Leg 2, which shall be detailed in forthcoming drawings.

Moving north above crease (122) is the third panel (140). This panel has two vertical perforated creases (indicated by dashes and circles). The west vertical crease (141) attaches to tab (143). The east vertical crease (142) attaches to tab (144). The TO address area (146) is on panel (140). This is the area whereby a manufacturer can place an individual address for delivery. A point for the manufacturer to consider is that the TO address area (146) could also be placed on the opposite side panel (120). The placement of the address (146) is at the discretion of the manufacturer. There is sufficient room on this panel (140) to also place postage in the top right corner (the north east corner). An area for postage was not specified on this drawing as it is up to the manufacturer if they wish to print a stamp, or a bar-code image, or embed a computerized chip. Therefore, it is by design that a minimal area has been indicated for an address. This address could be to an individual address or it could be to a business, such as a clinic, hospital, or office building, for example. North of (140) is horizontal crease (145) as indicated by dashed lines. North of (145) is the fourth panel (150), with a north horizontal crease (151). This panel will be part of a "valley fold", which will be detailed in forthcoming descriptions. Moving north above crease (151) is the fifth panel (160). The north perforated horizontal crease (161), as indicated by dashes and small circles. This panel also has an adhesion strip (162) and an adhesion cover (163). Moving north of perforated crease (161) is sixth panel/tab, (170).

MANUFACTURE OPTION- FLAT STORAGE: These drawings show how the device, MAILABLE INSPECTOR COLLECTOR, should be assembled for distribution. If, however, a manufacturer wishes to create these devices and store them in an unfolded flat state, then this "lab" or TEST PLATFORM (100) with all the elements attached, would require a protective sheet covering to keep the elements sanitary during storage and maintain the integrity of the adhesives. The protective sheet covering would need to cover all the elements either individually or the entire TEST PLATFORM (100). It would be needed to cover the exposed adhesive (FIG. 2, parts 271, 246, 245) for flat storage. It is the opinion of the inventor that the best way to store this device with a minimum amount of waste is in fully folded Leg 1 position where the TO address (146) is visible and the unit is in an easy-to-store stackable (equiangular quadrilateral/parallelogram) configuration.

MANUFACTUER OPTION-BUFFER: The manufacturer may consider the application of a buffer to the surface of the window of the PROTECTIVE TRANSPARENT VIEWER (109) as this set (108 and 109) shall fold along the hinge (110) on top of the elements to be analyzed. The buffer, referenced in section titled Elements Needed To Assemble Device Mailable Inspector Collector serves to act as the final element of analysis to solubilize the bio-sample. It is at the discretion of the manufacturer if they wish to coat this surface of the window (109) with such a buffer. It is at the manufacturer's discretion if they wish to provide instructions to the Test Subject to add the appropriate amount of liquid (e.g. purified water, etc.) at the appropriate time. Likewise, it is at the discretion of the manufacturer to consider also including a capsule like container of an appropriate substance to the surface of either the window frame (108) or the window pane (109) which, when the component flips over, is sealed around the analyzed bio-sample and is able to dissolve or be released with a bit of pressure to moisten the elements contained between the base of the TEST PLATFORM (100) and the window frame (108) and window (109) of the PROTECTIVE TRANSPARENT VIEWER (108 and 109). Likewise, it is at the discretion of the manufacturer to skip the buffer application altogether. This concludes description of FIG. 1.

Figure 2:
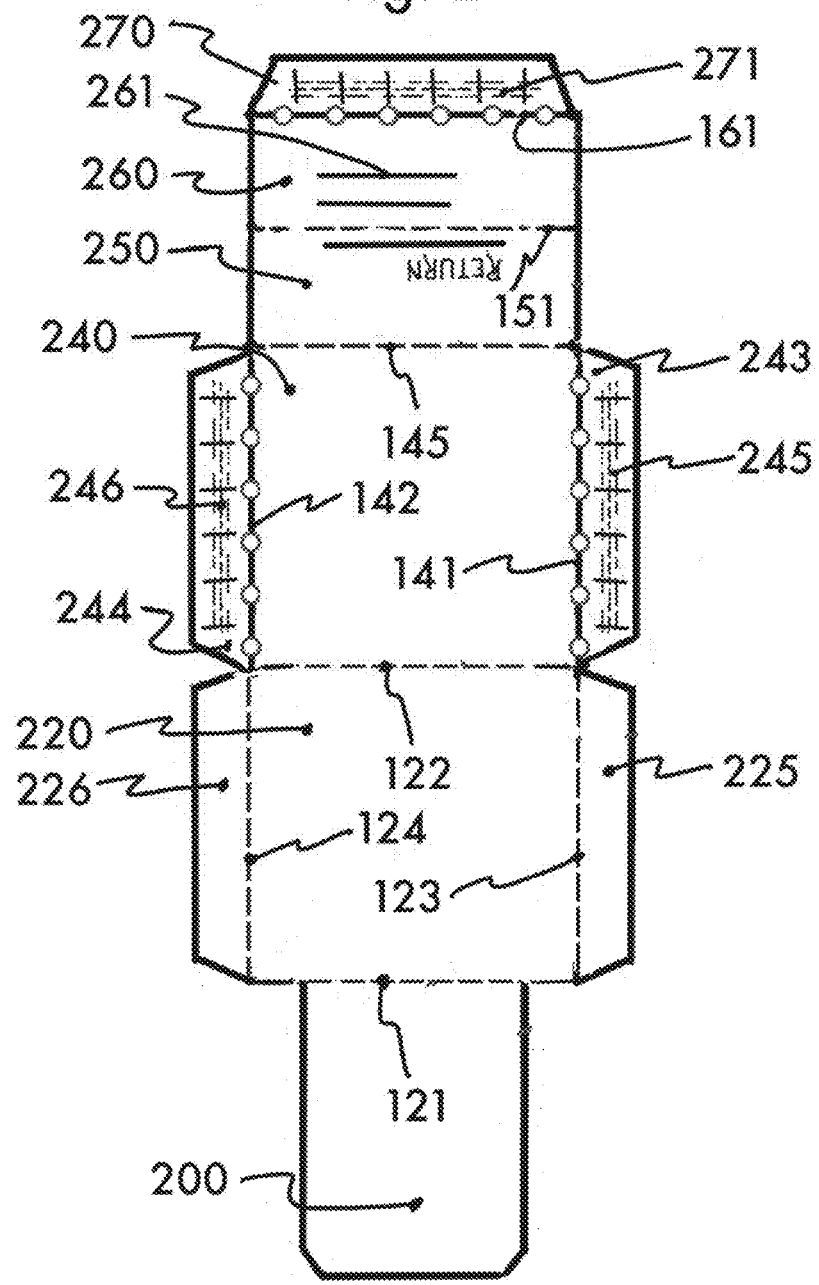

FIG. 2 Back flat view of unfolded device.

This FIG. 2 is the reverse side of FIG. 1. Starting from the very bottom first panel (200) is the back side of the TEST PLATFORM (FIG. 1, Part 100). To the north of panel (200) is crease (121), as indicated by a horizontal dashed line. Moving north of crease (121), is the second panel (220). The west side of which has a vertical crease (124) connected to a tab (226). The east side of panel (220) has a vertical crease (123) connected to a tab (225). The north side of this panel is bordered by a horizontal crease (122) as indicated by a horizontal dashed line.

Moving north of crease (122), is the third panel (240). The west side has a perforated vertical crease (142) which connects to tab (244) with a manufacturer adhesive (246) and no covering as it is intended that the manufacturing process also includes folding the device until Leg 1 preparations are completed. Likewise, the east side of the panel (240) has a perforated vertical crease (141) connected to tab (243) with manufacturer adhesive (245). Both vertical creases (141 and 142) are indicated by horizontal dashed lines with small circles, which represent tiny holes or perforations. Panel (240) is bordered by a north horizontal crease (145). Moving north of crease (145) is the fourth panel (250), bordered by a north horizontal crease (151). It is on this panel (250) that part of the RETURN address (261) may reside. Moving north of crease (151) is the fifth panel (260). This panel has part or all of the RETURN address (261). The north side of this panel (260) has a horizontal perforated crease (161) as indicated by dashes and small circles. Moving north of perforated crease (161) is the sixth panel (270). This panel contains a manufacturer adhesive (271). This concludes the description of FIG. 2.

Figure 3:
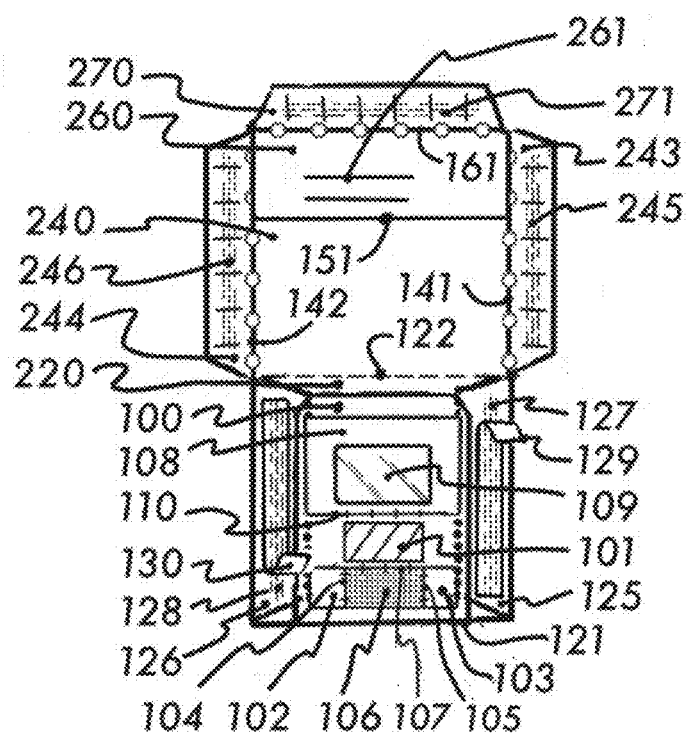

FIG. 3 Front flat view Manufacturer folding for Leg 1 Lab Visible.

This drawing shows the some of FIG. 1 and some FIG. 2. This figure shows the first five folds manufacturer needs to prepare Leg 1 before delivery to the Test Subject user. The TEST PLATFORM (100) folds and the valleyfold is created.
Fold 1: FIG. 2 Along Crease 123, Tab 225 folds to meet Panel 220.
Fold 2: FIG. 2: Along Crease 124, Tab 226 folds to meet Panel 220.
Fold 3: FIG. 2: Along Crease 121, Panel 200 folds to Panel 220.
To create the valleyfold: Fold 4: FIG. 2: Along Crease 145, Panel 250 folds onto Panel 240.
Fold 5 FIG. 1: Along Crease 151, Panel 160 folds onto Panel 150. This creates the "valley fold" which align two creases (145 and perforated crease 161).
The RETURN address area (261) is upside down on panel (260) from this perspective. The exposed manufacture adhesives are visible (245, 246, 271). All lab elements on TEST PLATFORM (100) are visible. This concludes the description of FIG. 3.

Figure 4:
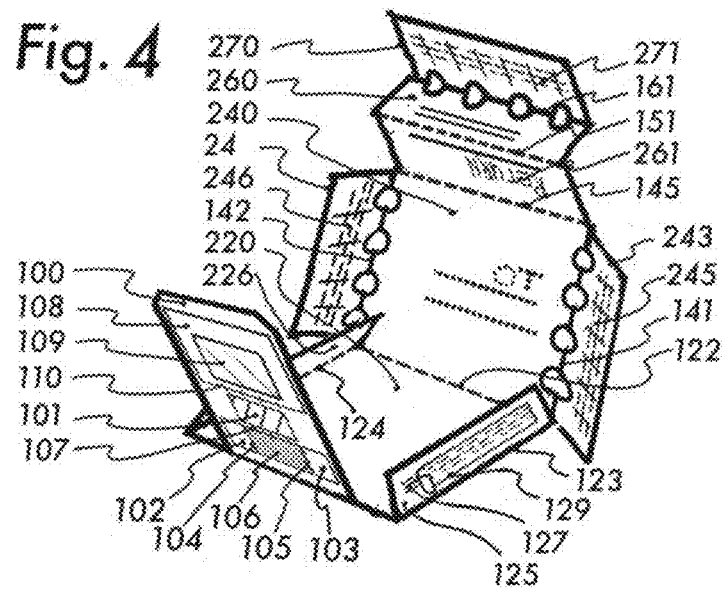

FIG. 4 Perspective of fold in progress for Leg 1

FIG. 4 shows a perspective of FIG. 3 with the folds to form the valleyfold at crease (151). TEST PLATFORM (100) and associated lab elements are visible. Also visible in this perspective is the folded RETURN address area (261) on panel (260) and perforated crease (161) as well as standard crease (151) which is now placed in the center of the partially hidden panel (240). To the north of perforated crease (161) is panel (270) which has the manufacturer adhesive (271). This concludes description of FIG. 4.

Figure 5:
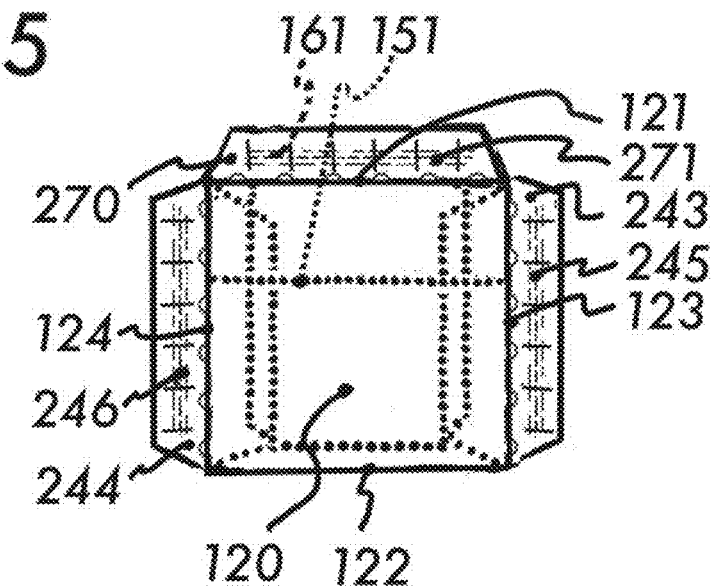

FIG. 5 Front flat view of folded device not yet sealed for Leg 1 (Continuation of FIG. 3)

FIG. 5 illustrates how the device is folded, but the three tabs are not yet sealed by the manufacturer for Leg 1 . . . Previously, the bottom panel from FIG. 3 folds northward along crease (122) to reveal panel (120). Visible are west tab (244) and manufacturer adhesive (246) protruding out from underneath crease (124); East tab (243) with manufacture adhesive (245), protruding out from underneath crease (123). From beneath crease (121) protrudes the top of the valleyfold revealing tab (270) with manufacture adhesive (271). Note that it is for the manufacture to decide if they wish to place the TO address (146) on panel (120). These exposed adhesives will be folded in a future drawing. This concludes the description of FIG. 5.

Figure 6:
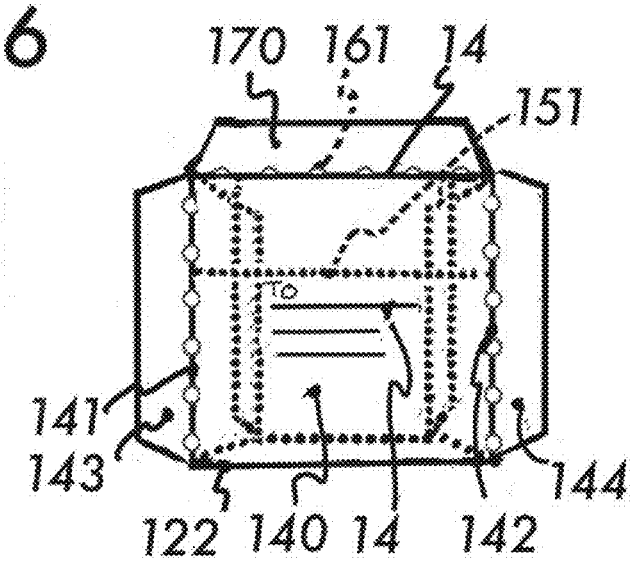

FIG. 6 Back flat view of folded device not yet sealed for Leg 1(Reverse of FIG. 5)

This FIG. 6 shows the third panel (140) with the TO address area (146) exposed (reverse side of Figure S) and not yet sealed. This concludes description of FIG. 6.

Figure 7:
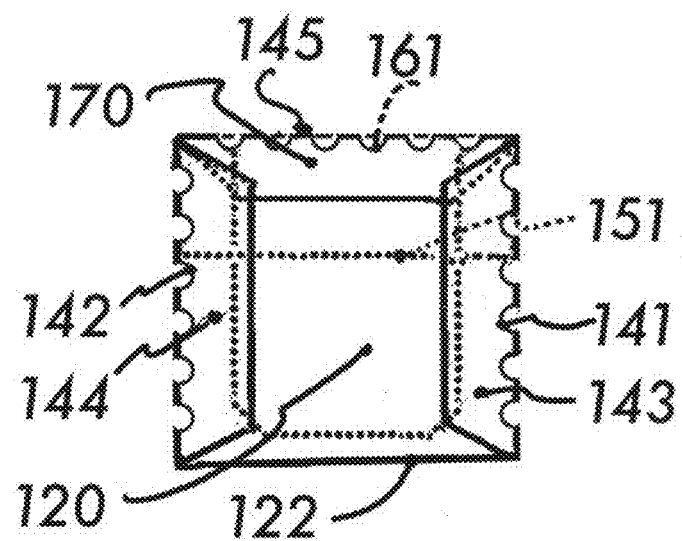

FIG. 7 Front flat view of folded and sealed device for Leg 1 (Continuation of FIG. 5)

This drawing is a continuation after Figure which shows a fully folded and sealed device. The manner in which to seal the tabs is in the following order: First, seal north horizontal tab (170). Second, seal west vertical tab (143) to overlap over the edge of tab (170). Third, seal east vertical tab (144) to overlap over the opposite edge of tab (170). Both tab (144) and tab (143) lie on top of horizontal tab (170), to lock in (170) and the hidden valley fold, which also hides crease (121), (145) and (161). This concludes the description of FIG. 7.

Figure 8:
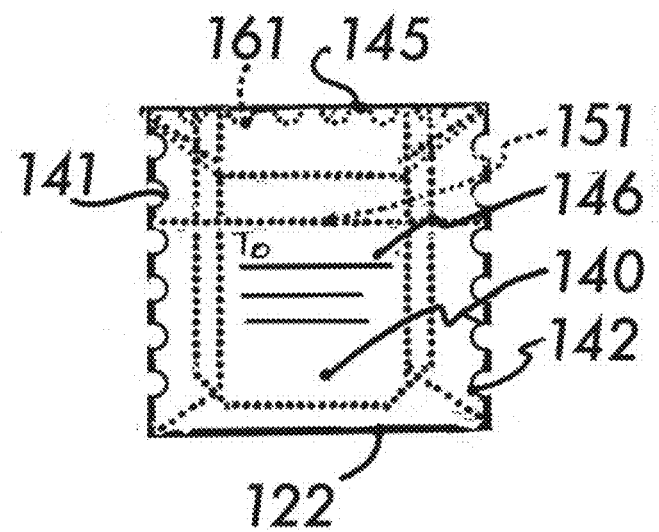

FIG. 8 Back flat view of folded sealed device for Leg 1 where TO: address is visible and device is ready to be mailed.—END of Leg 1 preparation. (Continuation of FIG. 6, Reverse of FIG. 7)

FIG. 8 shows the final step for the manufacturer to prepare the device for Leg 1, which means the device is ready to be placed in the mail as an individual unit or it may be bundled with other folded devices to be mailed in bulk. In this drawing, panel (140) is visible with TO address area (146). It is the intent of these perforated creases to remain sealed until it reaches the destination address, at which point the Test Subject will slit or open the selected three sides (Perforated creases: 141, 161, and 142) as depicted in FIG. 9. This completes the manufacturer preparation for mailing and is the end of Leg 1. This concludes the description of Drawing for FIG. 8.

FIG. 9: Test Subject opens three sides of device

This drawing shows how a Test Subject (person who will use the MAILABLE INSPECTOR COLLECTOR) would view the device once it arrived in the mail. This diagrams shows an image of a letter opener, which opens three sides so that the Test Subject may execute the first step of depositing a nasal-expressed bio-sample from their nostrils. The three sides could be slit with a letter opener or embedded string or some other mechanism to slit open at the three perforated creases (142, 161, 141). This drawings shows how the Test Subject will use the MIC device before the Test Subject must prepare the MAILABLE INSPECTOR COLLECTOR for Leg 2 mailing. The perforated edges are to be opened with a letter opener, pointed finger, pulling of a string, or other element, to split open perforated creases (141,142, 161) so that it opens like a clamshell along crease (122). Note that after the MAILABLE INSPECTOR COLLECTOR device is opened by the Test Subject, the tabs (144, 143, 170) will remain affixed to the surface of panel (120). This concludes the description of FIG. 9.

FIG. 10: Perspective view of opened device to reveal test platform

This drawing shows how the device appears to the Test Subject once it is opened. The TEST PLATFORM (100), which contains all associated lab elements, is folded along crease-hinge (121) so the TEST PLATFORM (100) lays flat as if the Test Subject is opening a clamshell hinged at crease (122). The position of the SAMPLE COLLECTOR nanostructure pad (106) is located closest to the edge of south crease (121). This is designed to that the Test Subject may position the nostrils on the nano-pad (106) without excess elements obstructing their mouth, upper face, etc. The Test Subject will deposit a bio-sample with the MIC device in the open-clamshell position shown. The slit-open perforated edges (141, 142, 161) are indicated by dashes and half-circles to show that the associated tabs (144, 143, 170) have been detached and are hidden in this drawing and remain affixed to panel 120. This completes the description of FIG. 10.

FIG. 11: Perspective of device being used by Test Subject (nose placement indicated)

This drawing depicts the nose placement on the SAMPLE COLLECTOR nano pad (106) so that the Test Subject nostrils are aligned with the nano-pad (106). The crease (121) may touch the upper lip region of the Test Subject during the bio-sample deposit process. The entire device is not shown. In this view the portions of the device which are shown are the exposed SAMPLE COLLECTOR handle (103) as the opposing SAMPLE COLLECTOR handle (102) is partially hidden in this perspective. A portion of the nano-pad (106) is partially obscured by the Test Subject nose. Also visible is the ANALYSIS PAD (101), as well as the PROTECTIVE TRANSPARENT VIEWER (108 and 109). Panel 100 is also visible in this drawing. The crease (122) is visible, as is the area behind the TEST PLATFORM (100), which is panel (220). On the left side of the figure is (tab 125, adhesive 127 and cover 129) and right side of the figure is (tab 126, adhesive 128 and cover 130). Part of panel (240) is visible with crease (122) and the torn perforated edges of former crease (142) and (141). This concludes the description of FIG. 11. This concludes the portion where the Test Subject deposits a nasal-sample with the MIC device before Leg 2 preparation.

FIG. 12 Perspective exploded view of folding test platform for start of Leg 2

This drawing shows the start of Leg 2 where the Test Subject prepares the device for delivery to the appropriate processing facility: data collection, recycling, disposal, etc. This is a perspective exploded view showing how the entire SAMPLE COLLECTOR pivots downward on horizontal hinge (107) to align the nano-pad (106/106B) atop of analysis pad (101). Likewise, at the appropriate time, the PROTECTIVE TRANSPARENT VIEWER (108, 109) will pivot upward along the horizontal hinge (110) to lay on top of nano-pad (106B) so that color change process initiates.

MANUFACTURER OPTION—Buffer: If the manufacturer selected to coat the window part (109) with a buffer or allow for a release of a buffer in an element attached to the window frame (108), then the manufacturer should also provide the Test Subject with instructions as to duration of time needed before "closing the window" of the PROTECTIVE TRANSPARENT VIEWER. Any buffering coating or buffer element with a release mechanism is not depicted in these drawings as it depends on the pathogen being detected if those additional elements should be included.

MANUFACTURER OPTION—Window Frame Seal: If the manufacturer opts to also coat the PROTECTIVE TRANSPARENT VIEWER frame (108) with a sealant, then said sealant should also be indicated and instructions for use to ensure a secure seal should also be included for the Test Subject understanding. If a sealant requires a protective covering to ensure the integrity of the sealant adhesive is maintained until use of the sealant, it is at the manufacturer's discretion to also provide an appropriate adhesive covering for the window frame (108) and window itself (109) not depicted in this drawing.

MANUFACTURER OPTION—computerized component. The manufacturer may wish install other computerized components on, in, embedded within, or in close proximity near the MIC device for other data collection purposes. For example, a global positioning system (GPS), navigational tracking, element of neural network artificial intelligence system for data analysis, classification, alert system, data logging, trending, relevant health data, relevant happenings, device integrity usability notifications, or a mechanism to support contact tracing, etc. Not depicted in this drawing.

MANUFACTURER OPTION—Butterfly Handles on SAMPLE COLLECTOR. The SAMPLE COLLECTOR width and length of the handles (102 and 103) is at the discretion of the manufacturer as they may wish to provide instructions to either pivot along horizontal hinge (107) flat "butterfly wings open" position, instruct folding in "butterfly wings closed" along vertical hinge (104, 105) while still exposing nano-pad (106) before pivoting along horizontal hinge (107). the tabbed handle wings (102, 103) may not obstruct the connection between (101) and (106) because finalized test results must be able to "seep upward" and be visible to a user on part (106B), through PROTECTIVE TRANSPARENT VIEWER window (109). This concludes the description of FIG. 12.

FIG. 13 Exploded flat view for Leg 2—First fold

This drawing shows the flat view of FIG. 12 with the entire lab elements on the TEST PLATFORM (100) after the SAMPLE COLLECTOR has pivoted down along hinge (107). The underside of the SAMPLE COLLECTOR nano pad (106B) now covers the ANALYSIS PAD (101). This concludes description of FIG. 13.

FIG. 14 Exploded flat view for Leg 2—Second fold

This drawing follows the configuration of FIG. 13. The final stage is to have the PROTECTIVE TRANSPARENT VIEWER window (109) pivot upward on horizontal hinge (110) to align and protect the contents of the layered non visible ANALYSIS PAD (101) which is covered by the SAMPLE COLLECTOR nano-pad (106), where underside (106B) is face up. Any color change or fluorescence should still be visible through the PROTECTIVE TRANSPARENT VIEWER window (109B). This concludes the description of FIG. 14.

FIG. 15 Front view test platform fold for Leg 2 (Continuation of FIG. 14)

This drawing follows FIG. 14. This shows how the Test Subject will flip the TEST PLATFORM (100) around crease (121) to lay face down on panel (120) after collapsing all lab elements in a layered stacked manner. The tabs which were previously hidden underneath the TEST PLATFORM (tab 125 and 126) are now unfolded and lay flat and panel (200) is now visible. Also visible are perforated torn edge of crease (161), the adhesive (162) with, cover (163) on panel (160). The "valleyfold" is now unfolded. South of panel (150) is horizontal crease (145). On panel (140) is the west torn perforated edge (141) and the east torn perforated edge (142). Also visible is the TO address area (146). This concludes the description of FIG. 15

FIG. 16 Back view for Leg 2 (Reverse of FIG. 15)

FIG. 16 is the backside of FIG. 15, where the. RETURN address area (261) is either all on panel (260) or split over panel (260) and panel (250) overlapping crease (151). This concludes the description of FIG. 16

FIG. 17 Front flat folded view for Leg 2 (Continuation of FIG. 15)

The bottom panel is folded upward along crease (122). Although the cover (163) appear in this drawing. This concludes description of FIG. 17.

FIG. 18 Back flat folded view for Leg 2 (Reverse of FIG. 17)

This drawing shows the reverse side of FIG. 17. Adhesive covers (129, 130) are visible. At this point all adhesive covers (163, 129, 130) may now be removed by the Test Subject. This concludes description of FIG. 18.

FIG. 19 Front flat fully folded for Leg 2—Return address visible (Continuation of FIG. 17)

This drawing shows the sealed device with the RETURN address area (261) visible and right side-up. Panel (150) and (160) together wraps around horizontal crease (145), and crease (121), and secured by hidden adhesive (162) which adheres to panel (220). The adhesives (127, 128) on tab (125, 126) fold to adhere to panel (240).

MANUFACTURER OPTIONS: The manufacturer may auto-generate the Leg 2—RETURN address (261) based on the Leg 1—TO address (FIG. 1, part 146). This concludes description of FIG. 19.

FIG. 20 Back flat fully folded for Leg 2 Sealed tabs visible (Reverse of FIG. 19)

This drawing shows the reverse side of FIG. 19. The north horizontal crease (145) connects to third panel (240) over which lays west tab (226) which wraps around the hidden vertical crease (142). East tab (225) wraps around the hidden vertical crease (141). The Test Subject is now ready to deposit the re-folded and sealed used MIC device into the appropriate drop-box for Leg 2 delivery. This concludes description of FIG. 20. This is the end of Leg 2

FIG. 21 Detached SAMPLE COLLECTOR in larger size for livestock use

This drawing shows the perspective of a detached SAMPLE COLLECTOR (shown is backside of SAMPLE COLLECTOR: handle 102B, handle 103B, nano-pad 106B) (Not Shown are parts frequently referenced in other drawings: handle 102, handle 103, vertical hinge 104, vertical hinge 105, nano-pad 106) which has been detached from the horizontal hinge area (107—not shown). This is made in a larger scale to accommodate a larger test subject (bovine livestock example depicted) nostrils. Hands (not shown) can hold the SAMPLE COLLECTOR handles (Shown: 102B, 103B) as the livestock or other animal breathes into the nano-pad (Shown: 106B). Likewise, this separated unit can also be affixed to the animal nostrils with a number of various harness options or with robotic assistance (not shown). After a sample has been collected, this detached element can align with an appropriately scaled ANALYSIS PAD (part 101—not shown) to effect inspection analysis for the presence of a pathogen as described earlier. In other words, by detaching the SAMPLE COLLECTOR nano pad (106/106B) and handles (102/102B, 103/103B), the device can still analyze when reattached for analysis. Likewise, both sides of the nano-pad (106/106B) can also be attached to a robotic arm or around a roller cylinder to collect pathogens which may live on the surface of objects (not shown) and then component nano-pad (106—not shown) may come into contact with the appropriately sized and treated ANALYSIS PAD (101—not shown) to complete analysis. This concludes the description of FIG. 21. This concludes the descriptions for all figures from FIG. 1 to FIG. 21.

Existing Elements

An existing element to this invention is a stiff folding mailer with adhesive sealed edges. The United States Post Office already has stipulations pertaining to a mailer. For more details on those requirements, please see the appropriate Post Office Guide to obtain the exact information.

New Elements

The new element in this invention is creating internal subcomponents which can be folded on top of one another which will serve to collect a bio-sample, and analyze it without complex equipment, and render a visual result rapidly, making this a candidate for testing which can be used in many geographic areas and administered to large groups of diverse Test Subjects.

The invention claimed is:

1. A device for detecting the presence of a pathogen comprising:
   1) a SAMPLE COLLECTOR for securing a sample, comprising an interwoven mesh oppositely electrostatically charged from target-pathogen to attract pathogen; and
   2) a ANALYSIS PAD for analyzing sample comprising of at least one chemical; and
   3) a PROTECTIVE TRANSPARENT VIEWER for viewing a test result comprising a transparent material with the ability to release a buffering agent if needed; and
   4) wherein the device folds at least one of a segment/panel, or a smaller segment/panel flap, by pivoting it around at least one axis (a horizontal axis or a vertical axis) to complete a pivot/fold, including a valley fold configuration; and
   5) wherein the device is either in an original state or in an interim state; and
   6) a RETURNABLE MAILER for folding a TEST PLATFORM (comprising a SAMPLE COLLECTOR, an ANALYSIS PAD, a PROTECTIVE TRANSPARENT VIEWER) comprising a mail-worthy sheet of stock material including a fold at the edge thereof, with each segment/panel separated by a creased axis whereby segment/panels may pivot/fold (e.g., the valley fold configuration which hides secondary address until it is unfolded in a LEG 2 re-delivery configuration), around the appropriate axis to be arranged into at least one of three configurations: a LEG 1, and a testing execution or a LEG 2 configuration;
   wherein a LEG 1 configuration has the article arranged to be delivered to a primary address via delivery infrastructure as a single unit or in a Flat Bulk or a Folded Bulk configuration; and
   wherein a testing execution configuration has the article arranged (in an original state or in an interim state configurations) in either a Human non-modular-configuration or an Animal/object modular configuration to capture/collect/track, measure/detect/test, sense/analyze if a pathogen (e.g. virus-based particle, etc.) is present; and/or
   wherein a LEG 2 configuration has the article arranged to be re-delivered to a secondary address via delivery infrastructure as a single unit or in a Flat Bulk or in a Folded Bulk; and/or
   wherein device parts are in an original state (no need for replacement parts) or in an interim state (in need of replacement parts).

2. A device as in claim 1, wherein the ANALYSIS PAD comprises material with at least one of the following: enzymes and/or probe(s), and/or primer(s) and/or buffer(s) and/or excipient(s), and/or other chemical(s) (e.g., isothermal assay methodology to render a visible color change or fluorescence as a reaction to a sample containing at least 21 pathogenic molecules).

3. A device as in claim 1, wherein the SAMPLE COLLECTOR comprises electrostatically charged material which attracts pathogen (e.g. virus-based particle, etc.) of opposite polarity (e.g., predominantly negatively charged virus attracted to nearby material, which is positively charged to isoelectric point of target pathogen); and/or collects sample in either the Human non-modular configuration or the Animal/object modular configuration with or without assistance of an external aid.

4. A device as in claim 1, wherein the SAMPLE COLLECTOR, the ANALYSIS PAD, the PROTECTIVE TRANSPARENT VIEWER are arranged specifically to allow for modular detachment and reattachment (i.e., the Animal/object modular configuration) to and from the TEST PLATFORM
(e.g., detach the SAMPLE COLLECTOR from the TEST PLATFORM to collect a sample then reattach the SAMPLE COLLECTOR to ascertain if pathogen is present in samples collected from Test Subjects such as Bos taurus [e.g., livestock, cattle], *Ovis aries* [e.g., sheep], *Sus* [e.g., swine, pigs], *Felis catus* [e.g., feline, cats], *Canis lupus familiaris* [e.g., canine, dogs], *Mustela erminea* [e.g., ermine, stoat], *Mustela vison* [e.g., mink], etc., as well as objects such as counter-tops, floors, walls, mail-pieces, grocery-bags, playground equipment, operating room equipment, public transportation interiors, classroom desks, etc.).

5. A device as in claim 1, wherein the device of claim 1 is further arranged in the Human non-modular configuration comprised of parts which do not detach from said device.

6. A device as in claim 1, wherein the device of claim 1 is further arranged into the Animal/object modular configuration, comprised of modular components which detach and re-attach to said device, wherein various sized Test Subjects may be accommodated using parts intended for a different size Test Subject (e.g., Livestock manager testing cattle in pasture, then needing to test a smaller sized herding dog); and/or
   wherein external aids operate in conjunction with the SAMPLE COLLECTOR (e.g. the SAMPLE COLLECTOR detached from device, attached to a glove or wand to manually swipe surfaces of patient examination chairs, then reattached to said device to complete analysis).

7. A device as in claim 1, wherein the PROTECTIVE TRANSPARENT VIEWER functions to:
   A) encase/encompass/cover/protect/secure sample collected via the SAMPLE COLLECTOR and the ANALYSIS PAD; and
   B) allows observation of the visible test results (e.g., color change and/or fluorescence excitation); and/or
   C) includes a mode whereby the buffering agent may be dispensed at the appropriate time to maintain integrity (e.g., stability of sample pH) and/or any other agent or excipient needed to complete test; and/or
   functions to secure/seal/preserve integrity of the SAMPLE COLLECTOR and the ANALYSIS PAD during transport via delivery infrastructure.

8. A device as in claim 1 further arranged into at least one of the following three configurations comprising:
   1) the LEG 1 folded delivery configuration to primary address, wherein device is further arranged to be delivered in folded single unit or grouped in bulk (i.e., the folded bulk or the flat bulk configuration) to be delivered via delivery infrastructure;
   2) the testing execution configuration, wherein device is further arranged to be either the human non-modular, where parts do not detach or the Animal/object modular, where parts may be detached and reattached so that a sample may be collected with or without an external aid (e.g., the SAMPLE COLLECTOR on robotic device to collect samples) to complete analysis;
   3) the LEG 2 folded re-delivery configuration to secondary address, using the same RETURNABLE MAILER, wherein device is further arranged to be delivered in folded single unit, or in the flat bulk or the folded bulk configuration, to be transported via delivery infrastructure.

9. A device as in claim 1, wherein device of claim 1 is configured to be used in the original stale or in the interim slate wherein;
   A) the original state which is in no need of replacement parts; or
   B) the interim state which is in need of replacement parts and is fully functional even if replaced parts are intended for different sized unit(s) or misaligned (e.g. the small horizontal SAMPLE COLLECTOR is reattached vertically to the larger ANALYSIS PAD, yet renders results).

10. A device as in claim 1, wherein the device of claim 1 is further arranged in two bulk delivery configurations comprising:
    A) the flat bulk configuration, wherein flat unfolded units are grouped into a larger single unit to be delivered via delivery infrastructure; and/or
    B) the folded bulk configuration, wherein single units are folded first, then grouped into a larger single unit (e.g., individual units are folded so that the folded unit is configured to have at least one straight edge such as equiangular/quadrilateral/parallelogram/rectangle/square configuration, then stacked to create a larger cube/pillar) to be efficiently sorted/routed/processed as mail-piece(s) by hand, by device actuated, manually or automatically, as a result of inspection or detection or measurement of some feature of the material or articles to arrive at a specified destination.

11. A method of providing the device of claim 1 to be configured in the valley fold configuration comprising the steps:
    1) lay the device plain-side up to prepare device for the LEG 1 configuration; and
    2) pivot/fold the southern most first segment/panel northward to meet the second segment/panel with the east and the west segment/panel flaps folded inward (toward user) and onto/adjacent to the exposed TEST PLATFORM; and
wherein the method further comprising at least one of the following steps:
    3) pivot/fold the northern segment/panels four, five and six down as if it were a single unit along the horizontal axis between the segment/panels three and four; and
    4) pivot/fold the segment/panels five and six north upward along the horizontal axis between the segment/panels four and five; and
    5) pivot/fold the already folded first and the second segment/panels together north upward along the horizontal axis crease between the segment/panels two and three; and
    6) verify the user sees the reverse of the segment/panel two and that the now folded segment/panel two covers the segment/panel three and the segment/panel five, leaving the northern most segment/panel flap six exposed; and
    7) pivot/fold the northern most segment/panel six southward along the horizontal axis between the segment/panel six and the segment/panel five down to cover the back of the segment/panel two wherein the valley fold has been completed as a method step for the LEG 1 configuration.

12. A method using the device of claim 1 comprising the following steps:
    1) the device is manufactured; and
    2) the device unit(s) is/are configured in the folded individual, flat bulk, or the grouped folded bulk configuration; and;

wherein the method further comprising at least one of the following steps:

3) the device unit(s) is/are stored;
4) the device unit(s) is/are then delivered to primary address in the LEG 1 configuration;
5) the device unit(s) is/are used in the testing execution configuration (the Human non-modular or the Animal/object modular configuration in the original state or the interim state);
6) used the device unit(s) is/are re-delivered to secondary address in the LEG 2 configuration using the same RETURNABLE MAILER; OR
7) used the device unit(s) is/are received at secondary address (e.g., processing center, scientific laboratory, data collection unit to analyze technology augmentations, recycling center, disposal center, etc.) via standard delivery infrastructure.

13. A device as in claim 1, wherein at least one sheet of stock material of said device may provide sufficient space for and/or protection of elements embedded on/in/within/nearby device to leverage at least one element of a neural network ARTIFICIAL INTELLIGENCE system, which mimics the operation of a human brain, which can evaluate vast amounts of data and extract relevant subsets, acting as a training mechanism which allows for the analysis of supplied data (with or without fuzzy logic knowledge processing) including but not limited to and comprising of;

1) use of geo-spatial global positioning system (GPS) technologies for navigational tracking; and/or
2) sending, receiving, analyzing relevant data; and/or
3) triggering the execution of notification alert(s) based on specific rules and/or parameters; and/or
4) confirming the integrity of said device during various stages (e.g., supply chain locations, device integrity, exposure to extreme elements and/or moisture levels, which could damage device, etc.) as defined by specific parameters; and/or
5) processing data per regulatory and/or compliance standards (e.g., Compliance with regulations such as European Union General Data Protection Regulations [GDPR] and/or Data Privacy Laws in the United States of America, such as the California Privacy Rights Act [CPRA], which enhances the, California Consumer Privacy Act [CCPA], which is a state statute intended to enhance privacy rights and consumer protection for residents of California, United States of America,) and/or handing of DNA records to and other related sensitive personal data associated with bio-sample collection and analysis; and/or
6) logging date and/or time and/or time zone pertaining to specific data-handling parameters (e.g., when test was executed then results produced); and/or
7) logging trends pertaining to other devices (e.g., send an alert if device has been rendered inoperable/useless and/or this is identified as a pattern at a specific location, and/or other devices delivered to locations nearby also have been rendered inoperable/useless); and/or
8) viral load has increased since last test to a predetermined threshold-level, which may require medical attention and/or dispatch appropriate medical personnel to specified address; and/or
9) Test Subject has opted out of health monitoring and/or has data handling requests associated to their bio-sample(s); and/or
10) correlation with other health records, for example as those curated by Test Subject's hospital, and/or the National Health Service in Europe, and/or data stored by the International Consortium for Personalised Medicine (ICPerMed), and/or other healthcare records; and/or
11) correlation with death records with cause of death to correlate if death was caused by pathogen-in-question and/or to halt mailing of future devices to said recipient; and/or
12) correlation with other devices which may be positive at the same time to ascertain if all parties attended an event which may have contributed to pathogen-spread, then trigger a process whereby recipients may be contacted to confirm/deny contact with others who may have attended same event and contributed to infection of specified recipient; and/or
13) generating reports and/or visualizations (e.g., trends, determining duration between the positive test result for a specific individual and when symptoms have been reported to ascertain the duration of incubation before symptoms present themselves, any large events which positive Test Subject attended, to ascertain if they may have infected others at that event, etc.); and/or
14) communicate with other relevant data source(s) to correlate data collected by device with other existing data source(s), as well as the physical integrity (e.g., extreme heat and/or cold and/or moisture/humidity, etc.) of device to protect and/or house the relevant artificial intelligence (e.g., computerized) components embedded in/on/within/nearby device; to further the effort of contact tracing and/or other related activities for the purposes of conveying data to a data collection processing destination in a manner whereby data conveyance is without a physical vehicle nor physical mechanism (e.g., wireless, etc.);

wherein artificial intelligence functionality enhances said device for the public good.

14. A device as in claim 1, wherein the protruding segment/panel flap(s) acts as a fastener, which rotate/pivot/hinge/fold/tuck around axis/fold/crease to secure one part of the device to another part for proper ordered alignment.

15. A method using the device of claim 1, wherein the device of claim 1 is further arranged into the first configuration LEG 1, and the second configuration testing execution, or the third configuration LEG 2;

1) the LEG 1 for delivery to primary address is configured arranging the device so the plain-side is facing the user with the TEST PLATFORM being the southern most segment/panel at the bottom, hereafter referred to as first (or one), as the segment/panels are numbered south (one) up northward sequentially so that the top northern most the segment/panel is referenced as the sixth (or six) segment/panel; and
2) pivot/fold the southern most segment/panel along the adjacent north axis crease between the segment/panel one and the segment/panel two north/upward to align with the second segment/panel located adjacent to and north of the first segment/panel to expose the TEST PLATFORM (so the user sees the SAMPLE COLLECTOR, the ANALYSIS PAD, the PROTECTIVE TRANSPARENT VIEWER); and
3) pivot/fold the east vertical segment/panel flap and the west vertical segment/panel flap up and inward onto the second segment/panel adjacent to or on top of the exposed TEST PLATFORM; and 4) create the valley fold so that the reverse of the second segment/panel is visible and covers the third and the fifth segment/panels; and 5) pivot/fold the northern most top sixth segment/panel southward along the horizontal axis between the segment/panels five and six so that the sixth segment/panel secures/adheres/fastens to the back of the second segment/panel; and 6) pivot/fold the east vertical segment/panel flap and the west vertical segment/panel flap to secure/adhere/fasten to the second segment/panel and/or cover a portion of the secured sixth segment/panel, such that the LEG 1 configuration has transformed from a flat pre-folded configuration to a the LEG 1 folded configuration ready for storage and/or delivery as a single unit or in the flat bulk or the folded bulk configuration via a standard delivery infrastructure; and/or wherein the method further comprises unfolding folded LEG 1 (primary address delivery) configuration into the testing execution (the Human non-modular or the Animal/object modular) configuration, comprising:

7) the testing execution configuration for Test Subject user to deposit sample onto the SAMPLE COLLECTOR; and 8) the SAMPLE COLLECTOR is in the Human non-modular configuration; and/or 9) the SAMPLE COLLECTOR is in the Animal/object modular configuration to detect pathogens associated with objects (e.g., counter-tops, floors, walls, mail-Pieces, packages, grocery-bags, playground equipment, flora/vegetation, operating room equipment, public transportation interiors) and/or animals (e.g., livestock, domestic pets, farmed animals, such as mink), and/or 10) the SAMPLE COLLECTOR may be used with or without the assistance of an external aid (e.g., attach the SAMPLE COLLECTOR to a robotic arm associated with a mail-sorting machine to verify pathogen-free surfaces on mail-Pieces, or attach the SAMPLE COLLECTOR to a mechanical device to collect sample from livestock nostrils while livestock is in a stall); and/or 11) pivot/fold the SAMPLE COLLECTOR toward the ANALYSIS PAD to make contact; and 12) pivot/fold the PROTECTIVE TRANSPARENT VIEWER to secure/adhere/fasten/protect both the SAMPLE COLLECTOR and the ANALYSIS PAD and/or dispense buffering agents such that the testing execution configuration has completed; and/or wherein the method further comprises folding the unfolded testing execution configuration into the LEG 2 configuration, comprising:

13) the LEG 2 for re-delivery to secondary address is configured by pivoting/folding the TEST PLATFORM approximately 360 degrees along the north axis between the segment/panel one and the segment/panel two to align with the second segment/panel so that none of the exposed TEST PLATFORM is visible to the user; and 14) pivot/fold the second segment/panel along the north horizontal axis between the segment/panel two and the segment/panel three to align with the third segment/panel; and 15) pivot/fold the fourth and the fifth segment/panels together as if they were a single segment/panel down southward along the south horizontal axis between the segment/panel four and the segment/panel three to align with and flatly adhere/fasten/secure to the second segment/panel (e.g. to expose secondary address); and 16) pivot/fold the east vertical segment/panel flap of the second segment/panel around the east vertical axis down and under (away from the user) to secure/adhere/fasten to the third segment/panel; and 17) pivot/fold the west vertical segment/panel flap of the second segment/panel around the west vertical axis down and under (away from the user) to secure/adhere/fasten to the third segment/panel such that the LEG 2 configuration (for re-delivery to secondary address) has completed; and/or wherein the method further comprises re-delivering LEG 2 configuration to a secondary address, comprising:

18) receive/intake unit(s) in the LEG 2 configuration re-delivered to secondary address via standard delivery infrastructure as a single individual unit or in bulk (i.e., the flat bulk or the folded bulk configuration); and 19) process (e.g., analyze, recycle, disposed of, etc.) device unit(s).

* * * * *